US008623652B2

(12) United States Patent
Steinmetz et al.

(10) Patent No.: US 8,623,652 B2
(45) Date of Patent: Jan. 7, 2014

(54) HOST-VECTOR SYSTEM FOR CLONING AND EXPRESSING GENES

(75) Inventors: Eric Steinmetz, Madison, WI (US); Ronald Godiska, Mount Horeb, WI (US); David A. Mead, Middleton, WI (US)

(73) Assignee: Lucigen Corporation, Middleton, WI (US)

( * ) Notice: Subject to any disclaimer, the term of this patent is extended or adjusted under 35 U.S.C. 154(b) by 556 days.

(21) Appl. No.: 12/755,235

(22) Filed: Apr. 6, 2010

(65) Prior Publication Data
US 2010/0255561 A1 Oct. 7, 2010

Related U.S. Application Data

(60) Provisional application No. 61/167,086, filed on Apr. 6, 2009.

(51) Int. Cl.
*C12N 15/70* (2006.01)
*C12N 15/00* (2006.01)
*C07H 21/04* (2006.01)

(52) U.S. Cl.
USPC .................. 435/476; 435/320.1; 536/23.1

(58) Field of Classification Search
None
See application file for complete search history.

(56) References Cited

U.S. PATENT DOCUMENTS

| | | | |
|---|---|---|---|
| 4,952,496 A | 8/1990 | Studier et al. | |
| 5,693,489 A | 12/1997 | Studier et al. | |
| 5,830,694 A | 11/1998 | Studier et al. | |
| 5,869,320 A | 2/1999 | Studier et al. | |
| 6,569,669 B1 | 5/2003 | Raleigh | |
| 6,709,861 B2 | 3/2004 | Mead et al. | |
| 7,560,264 B2 | 7/2009 | Studier | |
| 7,846,688 B2 * | 12/2010 | Gill et al. ................ | 435/69.1 |
| 2007/0292954 A1 | 12/2007 | Elledge | |
| 2008/0286749 A1 | 11/2008 | Fox et al. | |

FOREIGN PATENT DOCUMENTS

| | | |
|---|---|---|
| WO | WO 97/04110 | 2/1997 |
| WO | WO2005052151 * | 6/2005 |
| WO | WO 2008/073746 A2 | 6/2008 |

OTHER PUBLICATIONS

Calos et al. Mol Gen. Genet., 183(3):559-600, 1980.*
Olins et al. J. biol. Chem., 264 (29), 16973-16976, 1989.*
Kleter et al., Am. J. Pathology, 153, 6: 1731-1739, 1998.*
Altschul et al., (1990) "Basic local alignment search tool." *J. Mol. Biol.* 215(3): 403-10.
Angrand et al., (1999) "Simplified generation of targeting constructs using ET recombination." *Nucleic Acids Res.* 27(17):e16.
Aslandis and De Jong, (1990) Ligation-independent cloning of PCR products (LIC-PCR).: *Nucleic Acids Res.* 18: 6069-6074.
Beck et al., (1982) "Nucleotide sequence and exact localization of the neomycin phosphotransferase gene from transposon Tn5." *Gene* 19: 327-336.
Blommel et al., (2007) "Enhanced bacterial protein expression during auto-induction obtained by alteration of lac repressor dosage and medium composition." *Biotechnol. Prog.* 23(3): 585-598.
Blow, (2008) "Structural genomics: inside a protein structure initiative center." *Nature Methods* 5: 203-207.
Bolivar et al., (1977) "Construction and characterization of new cloning vehicles. II. A multi-purpose cloning system." *Gene* 2: 95-113.
Bubeck et al., (1993) "Rapid cloning by homologous recombination in vivo." *Nucleic Acids Res.* 21(15): 3601-3602.
Calos , (1978) "DNA sequence for a low-level promoter of the *lac* repressor and an 'up' promoter mutation." *Nature* 274: 762-765.
Chandonia and Brenner (2006) "The impact of structural genomics: expectations and outcomes." *Science* 311: 347-351.
Chen, E (1994) "Host strain selection for bacterial expression of toxic proteins." *Methods in Enzymology* 241: 29-46.
Cheng et al., (1994) "The Structure of bacteriophage T7 lysozyme, a zinc amidase and an inhibitor of T7 RNA polymerase." *Proc. Natl. Acad. Sci.* USA 91:4034-4038.
Cohen et al., (1973) "Construction of biologically functional bacterial plasmids in vitro." *Proc. Natl. Acad. Sci.* USA 70: 3240-3244.
Davanloo et al., (1984) "Cloning and expression of the gene for bacteriophage T7 RNA polymerase." *Proc. Natl. Acad. Sci.* USA 81: 2035-2039.
Dubendorff and Studier, (1991) "Controlling basal expression in an inducible expression system by blocking the target T7 promoter with *lac* repressor." *J. Mol. Biol.* 219: 45-59.
Glascock and Weickert, (1998) "Using chromosomal lacIQ1 to control expression of genes on high copy-number plasmids in *Escherichia coli.*" *Gene* 223: 221-231.
Godiska et al., (2005) "Beyond pUC: Vectors for Cloning Unstable DNA." In: Kieleczawa J, ed., *DNA Sequencing: Optimizing the Process and Analysis*, 1st edition. Jones and Bartlett Publishers, Inc., Sudbury, Massachusetts, pp. 55-76.
Hoffman et al., (1995) "Lactose fed-batch overexpression of recombinant metalloproteins in *Escherichia coli.* BL21(DE3): Process control yielding high levels of metal incorporated, soluble protein." *Protein Expr. Purif.* 6: 646-654.
Klock et al., (2008) "Combining the polymerase incomplete primer extension method for cloning and mutagenesis with microsequencing to accelerate structural genomics efforts." *Proteins* 71: 982-994.

(Continued)

*Primary Examiner* — Nancy T Vogel
(74) *Attorney, Agent, or Firm* — Daniel A. Blasiole; Joseph T. Leone; DeWitt Ross & Stevens SC

(57) ABSTRACT

A system for ligase-free cloning and/or expressing a target gene is described herein. A preferred version of the invention includes an *E. coli* host. The host preferably includes a T7 RNA polymerase gene comprising a T7gp1 coding sequence, a lacUV5 promoter, and a lac operator. The host preferably further includes a lacI gene comprising a lacI coding sequence with an ATG start codon, a promoter derived from the $lac^{q1}$ allele, and a translational enhancer derived from a 5' RNA leader sequence of T7 gene 10. The invention further includes a low-copy plasmid vector comprising a T7 promoter a lac operator operationally linked to the T7 promoter. The system is configured to inhibit target gene expression when uninduced and to permit gene expression upon induction by auto-induction.

21 Claims, 9 Drawing Sheets

(56) References Cited

OTHER PUBLICATIONS

Kuijper et al., (1992) "Functional cloning vectors for use in directional cDNA cloning using cohesive ends produced with T4 DNA polymerase." *Gene* 112: 147-155.
Lehmeier et al. (1992) "Tac promoter vectors incorporating the bacteriophage gene 10 translational enhancer sequence for improved expression of cloned genes in *Escherichia coli.*" *J Biotechnol.* 23: 153-165.
Li et al., (2007) "Harnessing homologous recombination in vitro to generate recombinant DNA via SLIC." *Nature Methods* 4: 251-256.
MacFerrin et al., (1990) "Overproduction and dissection of proteins by the expression-cassette polymerase chain reaction." *Proc. Natl. Acad. Sci.* USA 87: 1937-1941.
Miroux and Walker, (1996) "Over-production of proteins in *Escherichia coli*: mutant hosts that allow synthesis of some membrane proteins and globular proteins." *J Mol. Biol.* 260: 289-298.
Oliner et al., (1993) "In vivo cloning of PCR products in *E. coli.*" *Nucleic Acids Res.* 21: 5192-5197.
Olins et al., (1988) "The T7 gene 10 leader RNA, a ribosome-binding site that dramatically enhances the expression of foreign genes in *Escherichia coli.*" *Gene* 73: 227-235.
Olins et al., (1989) "A novel sequence element derived from bacteriophage T7 mRNA acts as an enhancer of translation of the *lacZ* gene in *Escherichia coli.*" *J Biol Chem.* 264: 16973-16976.
Payne et al., (1999) "Manipulating large genomic clones via in vivo recombination in bacteria." *J. Hum. Hypertens.* 13(12): 845-8.
Peranen et al., (1996) "T7 vectors with modified T7lac promoter for expression of proteins in *Escherichia coli.*" *Anal Biochem.* 236:371-373.
Posfai et al., (1997) "Versatile insertion plasmids for targeted genome manipulations in bacteria: isolation, deletion, and rescue of the pathogenicity island LEE of the *Escherichia coli* O157:H7 genome." *J. Bacteriol.* 179: 4426-28.
Roge et al., (2005) "Use of pIVEX plasmids for protein overproduction in *Escherichia coli.*" *Microbial Cell Factories* 4:18.
Rong et al., (1998) "Promoter specificity determinants of T7 RNA polymerase." *Proc. Natl. Acad. Sci.* USA 95: 515-519.
Rosenberg et al., (1987) "Vectors for selective expression of cloned DNAs by T7 RNA polymerase." *Gene* 56: 125-135.
Saiki et al., (1985) "Enzymatic amplification of beta-globin genomic sequences and restriction site analysis for diagnosis of sickle cell anemia." *Science* 230: 1350-1354.
Sambrook et al., eds. (1989)*Molecular Cloning: A Laboratory Manual*, Cold Spring Harbor Lab Publ., 11.51 (Copy Not Provided).
Studier et al., (1986) "Use of bacteriophage T7 RNA polymerase to direct selective high-level expression of cloned genes." *J. Mol. Biol.* 189: 113-130.
Studier et al., (1990) "Use of T7 RNA polymerase to direct expression of cloned genes." Methods in Enzymology 185: 60-89.
Studier, (2005) "Protein production by auto-induction in high density shaking cultures." *Protein Expression & Purification* 41: 207-234.
Summers, (1998) "Timing, self-control and a sense of direction are the secrets of multicopy plasmid stability." *Molecular Microbiology* 29: 1137-1145.
Yannisch-Perron et al., (1985) "Improved M13 phage cloning vectors and host strains: nucleotide sequences of the M13mp18 and pUC19 vectors." *Gene* 33: 103-119.
Bahl et al., (1977) "Minimal length of the lactose operator sequence for the specific recognition by the lactose repressor." Proc. Natl. Acad. Sci., vol. 74, No. 3, pp. 966-970.
Calos et al., (1981) "The DNA Sequence Change Resulting from the $I^{Q1}$ Mutation, which Greatly Increases Promoter Strength." Mol. Gen. Genet. 183:599-560.
Dhodda et al., "Novel Protein Purification System and Expression Strains." Lucigen Corporation, (2007).
Guss et al., (2008) "New methods for tightly regulated gene expression and highly efficient chromosomal integration of cloned genes for *Methanosarcina* species." Archaea 2, 193-203.
O'Donnell et al., (2000) "The Initiation Codon Affects Ribosome Binding and Translational Efficient in *Escherichia coli* of cI mRNA with or without the 5' Untranslated Leader." Journal of Bacteriology, vol. 183, No. 4, 1277-1283.
Reddy et al., (1985) "Translation efficient of the *Escherichia coli* adenylate cyclase gene: Mutating the UUG initiation codon to GUG or AUG results in increased gene expression." Proc. Natl. Acad. Sci., vol. 82, pp. 5656-5660.
Mead, (2006) "New Tools for DNA Cloning, Expression, and Analysis." International Plant & Animal Genome Conference (2008) Vendor Workshop: Lucigen. http://www.intlpag.org/2013/index.php/abstracts/abstracts-archive.
Wagner et al., (1994) "An Efficient Shine-Dalgarno Sequence but Not Translation Is Necessary for *lacZ* mRNA Stability in *Escherichia coli.*" Journal of Bacteriology, vol. 176, No. 6, pp. 1683-1688.

\* cited by examiner

Tight Control of Expression by Lac Repressor

−IPTG Inducer

| Gene | Expression |
|---|---|
| lacI | High |
| T7gp1 | − |
| Target | − |

FIG. 1A

Leaky Expression due to Insufficient Lac Repressor

−IPTG Inducer

| Gene | Expression |
|---|---|
| lacI | Low |
| T7gp1 | −/+ |
| Target | + |

FIG. 1B

Gene Expression Induced by IPTG

+IPTG Inducer

| Gene | Expression |
|---|---|
| lacI | High |
| T7gp1 | + |
| Target | + |

*LacI*$^{q1+En}$ allele of the present invention: promoter in bold underline; enhancer derived from the Gene 10 leader in *underlined italics*; *lacI* coding sequence in underline only, and tonB terminator in *lower case italics*.

| | | | | | |
|---|---|---|---|---|---|
| AGCGGCATGC | ATTTACGTTG | ACACCACCTT | TCGCGGTATG | GCATGATAGC | 50 |
| GCCCGGAAGG | T*TTTAACTAT* | *AGTAAGGAGT* | *CTAAGCATGA* | *AACCAGTAAC* | 100 |
| GTTATACGAT | GTCGCAGAGT | ATGCCGGTGT | CTCTTATCAG | ACCGTTTCCC | 150 |
| GCGTGGTGAA | CCAGGCCAGC | CACGTTTCTG | CGAAAACGCG | GGAAAAAGTG | 200 |
| GAAGCGGCGA | TGGCGGAGCT | GAATTACATT | CCCAACCGCG | TGGCACAACA | 250 |
| ACTGGCGGGC | AAACAGTCGT | TGCTGATTGG | CGTTGCCACC | TCCAGTCTGG | 300 |
| CCCTGCACGC | GCCGTCGCAA | ATTGTCGCGG | CGATTAAATC | TCGCGCCGAT | 350 |
| CAACTGGGTG | CCAGCGTGGT | GGTGTCGATG | GTAGAACGAA | GCGGCGTCGA | 400 |
| AGCCTGTAAA | GCGGCGGTGC | ACAATCTTCT | CGCGCAACGC | GTCAGTGGGC | 450 |
| TGATCATTAA | CTATCCGCTG | GATGACCAGG | ATGCCATTGC | TGTGGAAGCT | 500 |
| GCCTGCACTA | ATGTTCCGGC | GTTATTTCTT | GATGTCTCTG | ACCAGACACC | 550 |
| CATCAACAGT | ATTATTTTCT | CCCATGAAGA | CGGTACGCGA | CTGGGCGTGG | 600 |
| AGCATCTGGT | CGCATTGGGT | CACCAGCAAA | TCGCGCTGTT | AGCGGGCCCA | 650 |
| TTAAGTTCTG | TCTCGGCGCG | TCTGCGTCTG | GCTGGCTGGC | ATAAATATCT | 700 |
| CACTCGCAAT | CAAATTCAGC | CGATAGCGGA | ACGGGAAGGC | GACTGGAGTG | 750 |
| CCATGTCCGG | TTTTCAACAA | ACCATGCAAA | TGCTGAATGA | GGGCATCGTT | 800 |
| CCCACTGCGA | TGCTGGTTGC | CAACGATCAG | ATGGCGCTGG | GCGCAATGCG | 850 |
| CGCCATTACC | GAGTCCGGGC | TGCGCGTTGG | TGCGGATATC | TCGGTAGTGG | 900 |
| GATACGACGA | TACCGAAGAC | AGCTCATGTT | ATATCCCGCC | GTTAACCACC | 950 |
| ATCAAACAGG | ATTTTCGCCT | GCTGGGGCAA | ACCAGCGTGG | ACCGCTTGCT | 1000 |
| GCAACTCTCT | CAGGGCCAGG | CGGTGAAGGA | CAATCAGCTG | TTGCCCGTCT | 1050 |
| CACTGGTGAA | AAGAAAAACC | ACCCTGGCGC | CCAATACGCA | AACCGCCTCT | 1100 |
| CCCCGCGCGT | TGGCCGATTC | ATTAATGCAG | CTGGCACGAC | AGGTTTCCCG | 1150 |
| ACTGGAAAGC | GGGCAGTAAa | *gcagaaagtc* | *aaaagcctcc* | *gaccggaggc* | 1200 |
| *ttttgact* | (SEQ ID NO:4) | | | | |

HOST-VECTOR SYSTEM FOR CLONING AND EXPRESSING GENES

CROSS REFERENCE TO RELATED APPLICATIONS

This application claims priority under 35 USC §119(e) to U.S. Provisional Patent Application 61/167,086 filed Apr. 6, 2009, the entirety of which is incorporated herein by reference.

FIELD OF THE INVENTION

This invention provides an improved host-vector system to clone and express target protein-coding genes.

BACKGROUND

The expression of recombinant proteins for commercial production and biomedical research is a major undertaking in molecular biology. Recent efforts towards the development of "structural genomics," in which protein structures for entire genomes are to be determined, create increased demand for simple, high-throughput cloning/expression systems (Walhout et al., 2000; Chandonia and Brenner, 2006; Blow, 2008).

While a variety of host organisms have been used to produce foreign proteins, the most commonly employed microorganism is the gram-negative bacterium, Escherichia coli. A common limitation of recombinant protein expression in E. coli is the toxicity of overexpressed proteins (Chen, 1994; Miroux and Walker, 1996).

Inducible Expression of Recombinant Proteins in E. coli Plasmid Vectors:

Host-vector systems that allow tightly regulated, inducible gene expression in E. coli are greatly preferred. Many different strains of E. coli and several DNA cloning vectors for protein expression have been developed (Bolivar et al., 1977; Yannisch-Perron et al., 1985; Denhardt and Colasanti, 1988; Godiska et al., 2005). The most widely used recombinant DNA cloning systems for regulated expression of proteins in E. coli rely upon transcription using bacteriophage T7 RNA polymerase (Studier and Moffatt, 1986; Rosenberg et al., 1987).

T7 Expression Systems:

T7 plasmid expression systems take advantage of (1) the specificity of binding of T7 bacteriophage RNA polymerase to its cognate DNA promoter (Rong et al., 1998) and (2) the high efficiency of T7 RNA polymerase-catalyzed transcription (Davanloo et al., 1984). In order to minimize synthesis of potentially toxic gene products, expression vectors are constructed so that transcription of target genes is under the control of T7 promoters on multi-copy plasmids (U.S. Pat. No. 4,952,496 to Studier et al., 1990; U.S. Pat. No. 5,693,489 to Studier et al., 1997). Transcription from T7 promoters occurs only in bacterial strains engineered to overproduce T7 RNA polymerase.

To minimize expression of deleterious gene products, cloning of DNA fragments under the control of a promoter for T7 RNA polymerase is performed in E. coli host strains that lack the gene for the T7 RNA polymerase, T7 gene 1 (T7gp1$^-$). For downstream protein expression, the recombinant plasmid carrying the T7 promoter upstream of the target gene can be introduced into a second host strain which expresses T7 RNA polymerase. Although this dual-host strategy helps to limit unwanted expression of potentially toxic proteins, it also imposes a significant effort in terms of time and labor.

It is theoretically possible to design an improved plasmid host-vector system in which a single E. coli T7gp1$^+$ host strain is used for both DNA transformation and subsequent expression of target genes. However, such a cloning/expression vector system is practical only if gene expression can be maintained under tight repression prior to induction, and if such repression can be overcome effectively upon induction.

State-of-the-Art T7 Expression Systems are Leaky:

E. coli systems used for T7-based expression place the target genes in recombinant plasmids under transcriptional control of T7 RNA polymerase (Dubendorff and Studier, 1991; U.S. Pat. No. 4,952,496 to Studier et al., 1990; U.S. Pat. No. 5,830,694 to Studier and Dubendorff, 1998). Commonly used strains such as E. coli BL21(DE3) are lysogens of the bacteriophage λ derivative λDE3 (Studier and Moffatt, 1986). In these lysogenic strains, T7 gene 1 (encoding bacteriophage T7 RNA polymerase) is expressed from the lacUV5 promoter, a highly active variant of the E. coli lac promoter. If lac repressor protein (lacI gene product) is bound to the lac operator DNA, then transcription of T7gp1 by E. coli RNA polymerase is prevented. However, upon binding to an inducer, such as allolactose, isopropylthiogalactoside (IPTG), etc., the conformationally altered repressor-inducer complex dissociates from operator DNA, allowing RNA transcription to proceed.

In principle, expression of T7 RNA polymerase from lacUV5 promoters is selectively de-repressed upon addition of inducer to bacterial cells (Studier and Moffat, 1986; Rosenberg et al., 1987). However, in practice, the lacUV5 promoter is subject to considerable "leaky" expression—even in the absence of inducer. This leakiness can lead to buildup of toxic gene products and instability of T7 expression vectors in host E. coli strains prior to induction (Studier et al., 1990; Chen, 1994; FIG. 1).

Strategies to Minimize Leaky Expression in T7 Plasmid Cloning Vectors:

One strategy employed to limit "leaky" expression of T7 promoter-dependent target genes is to augment transcriptional control by positioning a lac operator sequence adjacent to plasmid T7 promoters. Transcription from such T7-lac hybrid promoters is largely inhibited when the lac repressor protein occupies the operator (Dubendorff and Studier, 1991).

Unfortunately, the introduction of multi-copy plasmids containing T7-lac promoters into E. coli cells increases the number of lac operator DNA sequences. As a result, endogenous lac repressor protein, which is normally present at about ten copies per cell, is titrated. In the absence of sufficient lac repressor protein, both the lacUV5 promoter controlling T7 RNA polymerase and the T7-lac promoter controlling the expression of the target protein become derepressed.

In order to ensure that sufficient lac repressor is available to maintain repression of T7-lac and lacUV5 promoters, several strategies have been employed to increase lac repressor expression in the host cell. One strategy of increasing lac repressor expression is by incorporating high-expressing alleles of the lacI gene into the T7-lac expression vector (Dubendorff and Studier, 1991; Peranen et al., 1996). Mutant alleles of the lacI promoter have been described which express elevated levels of lac repressor protein. One such allele, lacI$^q$, contains a single point mutation in the −35 promoter element of lacI which increases the amount of lac repressor protein by 10-fold, as compared to wild-type E. coli (Calos, 1978; U.S. Pat. No. 6,569,669 to Raleigh). For low-copy vectors maintained at ~20 copies/cell, the combination of increased transcriptional activity of the lacI$^q$ promoter and increased copy number of the repressor gene is expected to result in a level of lac repressor that is ~200-fold higher than is normally produced from a single chromosomal copy of wild-type lacI. This increased level of repressor protein is expected to provide for tighter repression of target genes under control of a T7-lac promoter.

However, increasing the expression of the lac repressor protein to minimize background expression can be detrimental to protein production under certain modes of induction. Studies have shown that high levels of lac repressor protein resulting from the lacI$^q$ allele reduce the ability to induce protein expression through auto-induction (Blommel et al., 2007 and U.S. Pub. No. 2008/0286749 to Fox et al.).

Thus, a delicate balance between the lac repressor expression level and the number of lac operator sites must be attained for a system to both minimize background expression under uninduced conditions and permit acceptable expression levels upon induction for use with a variety of modes of induction.

SUMMARY OF THE INVENTION

A preferred version of the invention includes an *E. coli* host. The host includes a T7 RNA polymerase gene comprising a T7gp1 coding sequence operationally linked to a lacUV5 promoter, the latter of which comprises a lac operator. The host further includes a lacI gene comprising a lacI coding sequence with an ATG start codon, wherein the lacI gene is operationally connected to a promoter from the lac$^{qI}$ allele and a translational enhancer derived from a 5' RNA leader sequence of T7 gene 10, and wherein the lacI gene includes transcriptional terminators derived from the tonB gene. This lacI gene is referred to herein as the lacI$^{qI+en}$ allele (FIGS. 3 and 4). The preferred version of the invention further includes a low-copy plasmid vector comprising a T7 promoter upstream of a target gene insertion site and a lac operator operationally linked to the T7 promoter (FIG. 5).

The present invention effectively prevents the leaky background expression present in conventional T7 systems. Controlling factors involved in T7-lac expression systems is depicted in FIGS. 1A-1C. As shown in FIG. 1A, tight control of T7gp1 and target gene expression is achieved when sufficient lac repressor (lacI) is present in cells, so that chromosomal lacUV5 and plasmid T7-lac promoters are turned off. As shown in FIG. 1B, if insufficient lac repressor is present in the cells, limited transcription from lacUV5 promoter results in expression of the T7gp1 gene and production of T7 RNA polymerase. The expressed T7 RNA polymerase binds to T7-lac promoters on the plasmid, resulting in limited synthesis of plasmid-encoded gene products. This "leaky" expression of target genes is an unwanted property of many T7 expression systems. As shown in FIG. 1C, induction involves binding of an inducer (IPTG) to the lac repressor, resulting in an altered lac repressor conformation that inhibits binding of the lac repressor to DNA. The repressor-IPTG complex dissociates from lac operator DNA, thereby activating transcription from lacUV5 and T7-lac promoters.

The tight control of gene expression as achieved by the present system is depicted in FIGS. 2A and 2B. As shown in FIG. 2A, the genetic composition of the present system results in production of lacI repressor at sufficiently high levels to tightly inhibit transcription of T7gp1 and target genes in the absence of an inducer. Specifically, in the absence of inducer (depicted as IPTG), the abundant intracellular lac repressor binds to the lac operators controlling expression from the lacUV promoter and the T7 promoter. As a result, neither T7 RNA polymerase nor the target protein is produced in uninduced cells. If sufficient inducer is present, as shown in FIG. 2B, then the conformationally altered lac repressor-inducer complex dissociates from the lacUV5 promoter, allowing synthesis of T7 RNA polymerase and transcription of target genes from T7-lac promoters.

In addition to preventing background expression, the present invention also permits sufficient protein production after induction, particularly in the case of auto-induction.

Thus, the present invention produces an amount of lac repressor to properly balance between repression of expression in the uninduced state and induction of protein expression in the induced state, particularly with auto-induction.

The objects and advantages of the invention will appear more fully from the following detailed description of the preferred embodiment of the invention made in conjunction with the accompanying drawings.

BRIEF DESCRIPTION OF THE DRAWINGS

FIG. 1A depicts factors involved in tight control of target protein expression in T7-lac expression systems.

FIG. 1B depicts factors involved in leaky control of target protein expression in T7-lac expression systems.

FIG. 1C depicts factors involved in inducing target protein expression in T7-lac expression systems.

FIG. 4 depicts the nucleic acid sequence of the lac$^{qI+En}$ allele of the present invention (SEQ ID NO:4).

DETAILED DESCRIPTION OF THE INVENTION

Figure 2A:
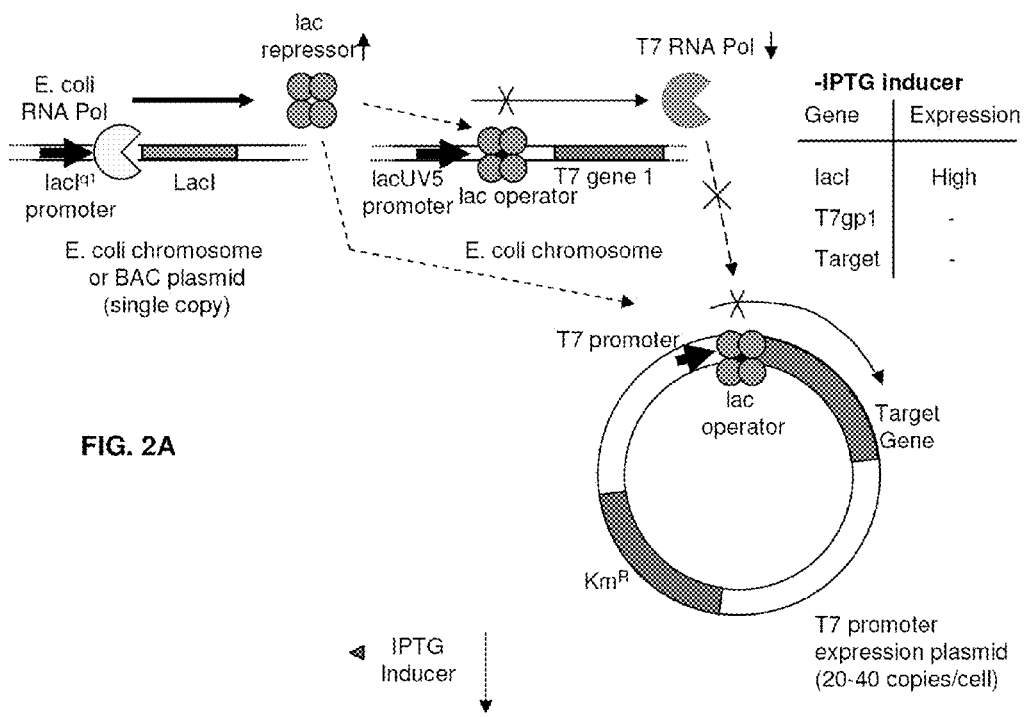
FIG. 2A depicts mechanisms involved in tight control of target protein expression in a T7-lac expression system of the current invention.
Figure 2B:
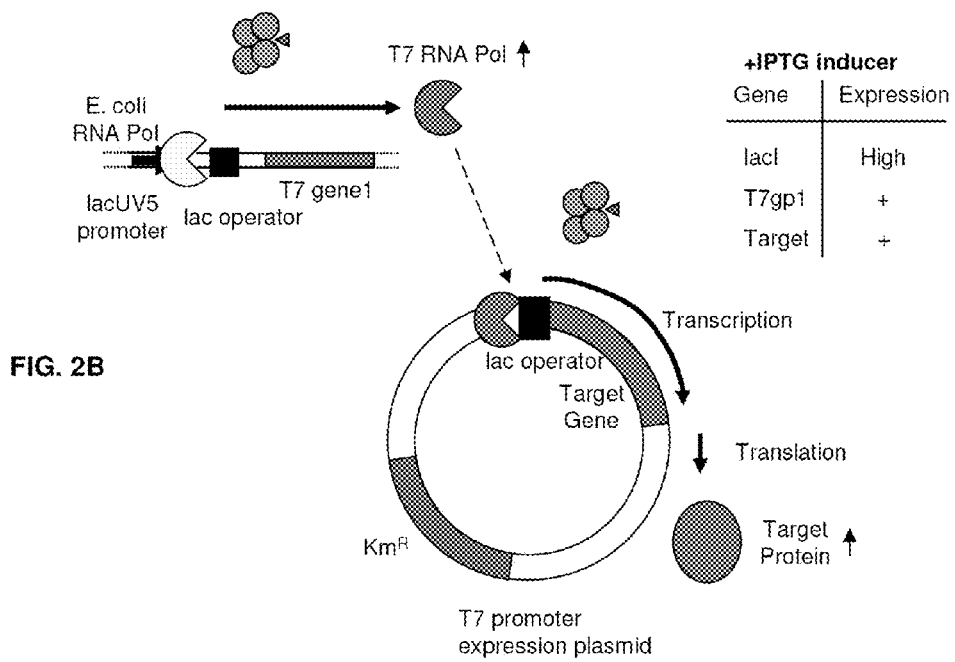
FIG. 2B depicts mechanisms involved in induction of target protein expression in a T7-lac expression system of the current invention.

The system described herein includes a host. "Host" refers to a prokaryotic organism capable of containing, or hosting, a plasmid artificially constructed using techniques well known in molecular biology. Examples include *Escherichia, Salmonella, Bacillus, Clostridium, Streptomyces, Staphyloccus, Neisseria, Lactobacillus, Shigella,* and *Mycoplasma*. *E. coli* strains include BL21(DE3), C600, DH5αF', HB101, JM83, JM101, JM103, JM105, JM107, JM109, JM110, MC1061, MC4100, MM294, NM522, NM554, TGI, $\chi^{1776}$, XL1-Blue, and Y1089$^+$, all of which are commercially available. Hosts used in the present invention are capable of accommodating nucleic acid constructs for cloning and/or expressing proteins that the constructs encode. Preferred hosts include λDE3 lysogens of *E. coli*, such as BL21(DE3). The same host in the present invention can preferably be used for both recombinant DNA cloning and protein expression.

The host preferably comprises a T7 RNA polymerase gene configured to produce a T7 RNA polymerase protein. The T7 RNA polymerase gene preferably includes a T7 RNA polymerase coding sequence, a promoter operationally linked to the T7 RNA polymerase coding sequence, and a lac operator operationally linked to the promoter. The T7 RNA polymerase gene is preferably incorporated into the host's chromosomal DNA or contained on a single-copy vector.

"T7 RNA polymerase gene" refers to any gene that expresses the T7 RNA polymerase enzyme or variants thereof which are capable of polymerizing RNA after binding to the T7 promoter. Exemplary coding sequences of a T7 RNA polymerase are provided by GenBank Accession No. M38308.1, the coding sequence for the T3/T7-like RNA polymerase encoded by T7 gene 1 (T7gp1; SEQ ID NO:8 for nucleic acid sequence and SEQ ID NO:9 for protein sequence), and variants thereof.

"Promoter" refers to a DNA sequence, normally located upstream of a protein-coding sequence, which contains a binding site for an RNA polymerase. The promoter for the T7 RNA polymerase is preferably structured to enable transcription by machinery comprised within the host. The promoter may include, for example, the *E. coli* lac promoter. A preferred promoter is the lacUV5 promoter or variants thereof, an exemplary version of which is provided by SEQ ID NO:1.

"Operationally linked" generally refers to the association of nucleic acid sequences on a single nucleic acid fragment so that the function of a first sequence is regulated by the a second sequence. In the context of a promoter being operationally linked to a coding sequence, the promoter is capable of regulating the expression of that coding sequence, i.e., the coding sequence is under the transcriptional control of the promoter. Coding sequences can also be operationally linked to regulatory sequences (such as enhancers) in a sense or antisense orientation.

"Lac operator" refers to a DNA sequence that binds to the lac repressor. Sequences of lac operators are well known in the art. Exemplary lac operator sequences are provided by SEQ ID NO:2; nucleotides 22-43 of SEQ ID NO:1, and nucleotides 71-88 of SEQ ID NO:7. "Operationally linked" in the context of a lac operator being operationally linked to a promoter refers to the ability of the lac operator to regulate the ability of the promoter to control expression of the coding sequence under specific conditions, such as ability of the lac operator to inhibit promoter-dependent expression of the T7 RNA polymerase gene when lac inhibitor protein is bound thereto. The lacUV5 promoter as depicted provided by SEQ ID NO:1 includes a lac operator (nucleotides 22-43 of SEQ ID NO:1).

Figure 3:
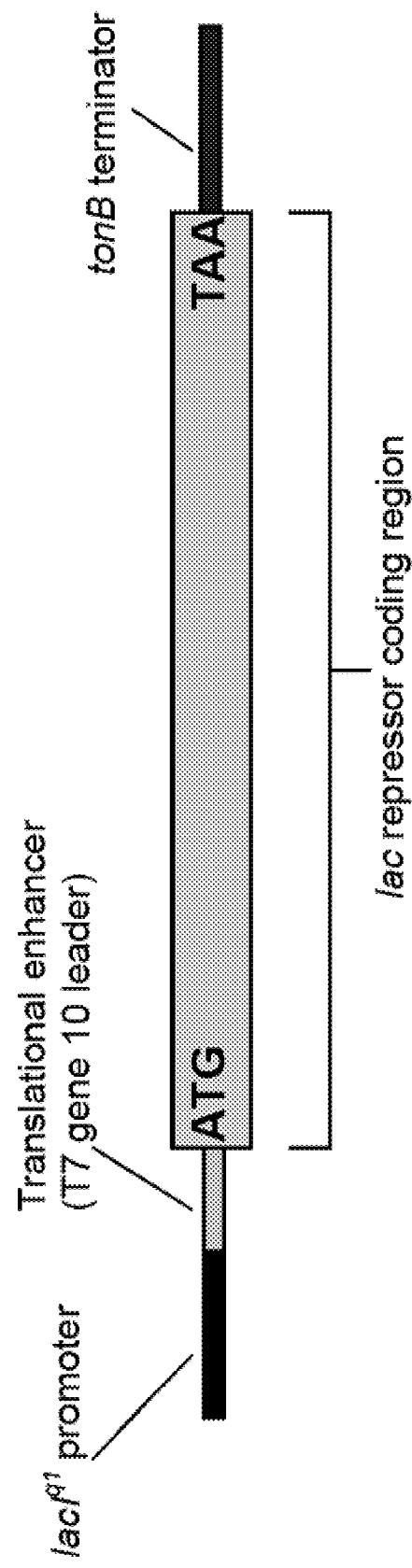
FIG. 3 depicts a schema of the lacI$^{qI+En}$ allele of the present invention.

The host also preferably includes a lacI gene. "LacI gene" refers to any gene that expresses the lac repressor protein or any variants thereof which are capable of binding to the lac operator. In a preferred version, the lacI gene includes a lacI coding sequence, a promoter operationally linked to the lacI coding sequence, and a translational enhancer sequence. A schema of an exemplary lacI gene (i.e., lacI$^{q1+En}$ allele) is depicted in FIG. 3. An exemplary nucleic acid sequence of a lacI gene (i.e., lacI$^{q1+En}$ allele) is depicted in FIG. 4 and is included herein as SEQ ID NO: 4. Variants of the lacI gene of SEQ ID NO:4 are also included in the invention. The lacI gene is preferably incorporated into the host's chromosomal DNA or contained on a single-copy vector.

The lacI coding sequence may begin with any initiation codon, including the GTG found in the native *E. coli* lacI coding sequence or ATG. The preferred version of the lacI coding sequence includes an ATG initiation codon. An exemplary lacI coding sequence is shown in FIG. 4 (nucleotides 87-1169 of SEQ ID NO:4). Variants of the lacI coding sequence in SEQ ID NO:4 are also included in the invention. The polypeptide product encoded by the coding sequence of SEQ ID NO:4 is provided by SEQ ID NO:5.

The promoter for the lacI coding sequence may include the native lacI initiation codon or any variants thereof, such as the promoter (SEQ ID NO:6) of the lacI$^q$ allele (Glascock and Weickert, 1998). The lacI$^q$ promoter includes a point mutation in the promoter region upstream of the native lacI gene, resulting in a 10-fold increase in mRNA transcription. A preferred version of the invention includes the promoter (nucleotides 1-56 of SEQ ID NO:4) on the lacI$^{q1}$ allele. See FIG. 4. The lacI$^{q1}$ promoter comprises a deletion in the −35 regions upstream of the lacI gene. The resulting substitution of upstream sequences into the −35 region results in a 100- to 200-fold increase in mRNA transcription.

"Translational enhancer" refers to any sequence known or discovered in the art that increases the efficiency of translation of protein from mRNA. The translational enhancer sequence is preferably derived from the translational enhancer derived from the 5' RNA leader sequence of T7 gene 10. An exemplary version of the translational enhancer sequence is shown in FIG. 4 and is provided by nucleotides 62-71 of SEQ ID NO:4. Variants of the translational enhancer sequence shown in SEQ ID NO:4 are included in the present invention. Exemplary variants include TTAACTTTA, TTAACTT, TTAACT, ACTTTA, AATTTTA, GGCTTT, AACTTTG, AACTTT, and TAACTTTA. The translational enhancer is preferably disposed in the lacI gene between the promoter and the coding sequence.

Some versions of the lacI gene include transcriptional terminators derived from specific sources. In a preferred version, the lacI gene includes a transcriptional terminator derived from the tonB gene of *E. coli*. An exemplary version of a tonB terminator is shown in FIG. 4 and provided by nucleotides 1170-1208 of SEQ ID NO:4.

The T7 RNA polymerase gene and the lacI gene are preferably integrated into the host's chromosomal DNA or harbored on a single-copy plasmid such as a bacterial artificial chromosome (BAC). Integration of the genes into the host's chromosomal DNA can be introduced by restriction enzyme-mediated cloning strategies, PCR-based cloning strategies, or allele replacement methods (e.g., Angrand et al., 1999, Payne et al., 1999, and Posfai et al., 1997). Introduction of the BAC into the host can be performed as described in U.S. Pat. No. 6,569,669.

The genetic elements included in a single copy of the lacI gene of the present invention preferably provide for increased expression of the lac repressor protein compared to the wild-type *E. coli* lacI gene. Various versions of the lacI genes of the present invention, when present in a host in a single copy, increase lac repressor protein expression of at least about 2-fold, 5-fold, 10-fold, 50-fold, 100-fold, 200-fold, 300-fold, or 400-fold compared to the wild-type *E. coli* lacI gene. The degree of the increase in a particular version, however, may vary according to downstream uses. The amount of lac repressor protein in the cells is preferably high enough to substantially inhibit background expression of the recombinant gene in uninduced conditions while permitting a significant increase in expression of the recombinant gene upon induction. This is structurally a result of lac repressors being bound to substantially all (or at least a large majority) of lac operators in the uninduced state (i.e., in the absence of inducer) and lac repressors dissociating from substantially all (or at least a large majority) of the lac operators in the induced state (i.e., in the presence of inducer). The amount of lac repressor protein in the cells preferably permits an increase in expression of the recombinant gene of at least about 10 fold, 25 fold, 50 fold 100 fold, 200 fold, 300 fold, 400 fold, 500 fold, 600 fold, 800 fold, 1000 fold or more upon induction.

Figure 5:
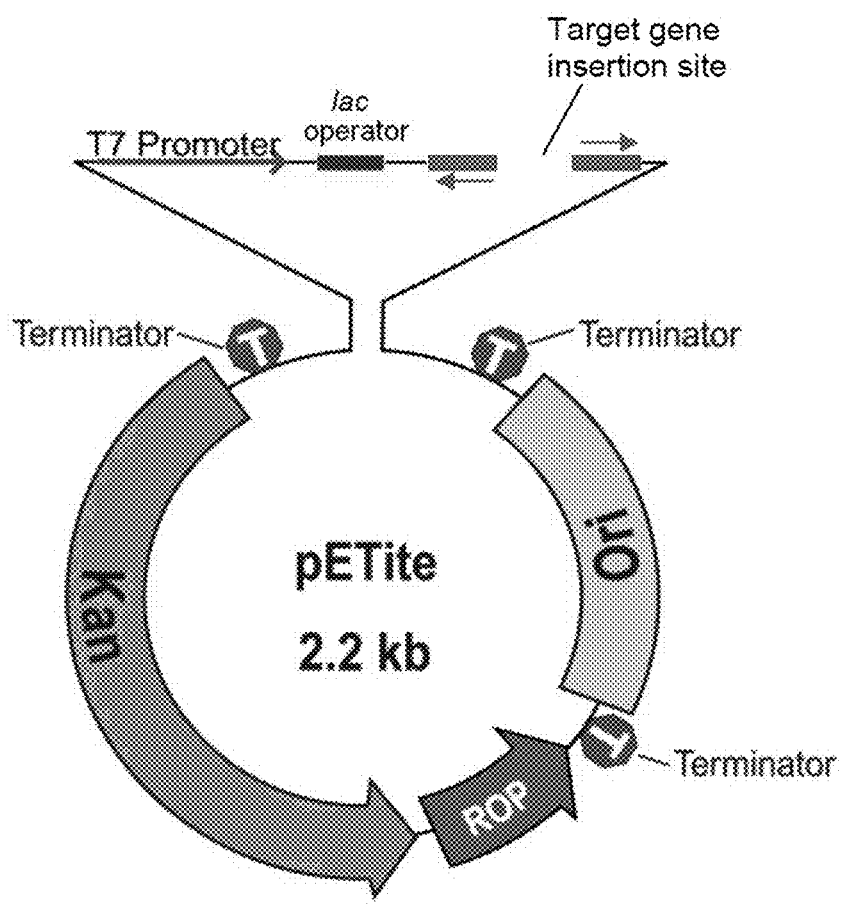
FIG. 5 depicts a plasmid vector of the present invention.

In some versions, the system further includes a T7 plasmid vector. "T7 plasmid vector" refers to any extrachromosomal DNA molecule capable of replicating independently from chromosomal DNA, capable of harboring a recombinant target gene, and capable of expressing the recombinant target gene under the control of a T7 promoter. The target gene includes, without limitation, any gene intended to be cloned, recombined, and/or expressed in the host. The gene product produced from the target gene is referred to herein as "target protein." The T7 plasmid vectors of the present invention preferably include a target gene insertion site, a T7 promoter operationally linked to the target gene insertion site, a lac operator operationally linked to the T7 promoter, and/or an antibiotic-resistance marker gene. A schematic illustration of an exemplary T7 plasmid vector ("pETite") is presented in FIG. 5. An exemplary sequence of a T7 plasmid vector ("PETite") is provided in SEQ ID NO:7. A T7 promoter operationally lined to a lac operator is referred to herein as a "T7-lac" promoter.

The target gene insertion site includes a nucleotide sequence suitable for incorporation of a target gene. Sequences suitable for incorporation of target genes are known in the art and include but are not limited to multiple cloning sites. Exemplary gene insertion sites include between nucleotides 145 and 146 and between nucleotides 163 and 164 in SEQ ID NO:7, depending whether a C-terminal His6 tag or an N-terminal His6 tag, respectively, is desired.

The T7 promoter of the present invention preferably comprises the sequence as provided in SEQ ID NO:3, nucleotides 51-70 of SEQ ID NO:6, or variants thereof, and is disposed upstream of the target gene insertion site. Any variants of the T7 promoter must maintain the ability of the T7 RNA polymerase to bind thereto. "Operationally linked" used with reference to the T7-lac promoter being operationally linked to the recombinant gene insertion site refers to the ability of the T7-lac promoter to drive expression of a gene inserted in the recombinant gene insertion site through activity of the T7 RNA polymerase.

The lac operator operationally linked to the T7 promoter preferably includes the lac operator sequences as described herein, or variants thereof. "Operationally linked" used with reference to the lac operator being operationally linked to the T7 promoter refers to the ability of the lac operator to regulate the ability of the promoter to control expression of the coding sequence under specific conditions, such as ability of the lac operator to inhibit promoter-dependent expression of the target gene when lac inhibitor protein is bound thereto.

"Antibiotic resistance marker gene" refers to a gene whose encoded gene product confers resistance to one or more antibiotics when expressed in a host cell (and its progeny). The definition explicitly includes any antibiotic resistance marker now known or developed in the future, including (without limitation) markers that confer resistance to ampicillin (e.g., beta-lactamase [bla, TEM-1]), hygromycin (e.g., hygromycin phosphotransferase [aphIV, hpt, hph]), kanamycin and/or neomycin (e.g., neomycin phosphotransferase II [nptII, APH (3')-II]), chloramphenicol (e.g., chloramphenicol acetyltransferase [$cm^R$, cat]), tetracycline ($tet^R$), and the like. Inclusion of an antibiotic resistance marker gene on the T7 plasmid vector permits selection of hosts harboring the plasmid with the appropriate antibiotics. In the preferred version of the invention, the T7 plasmid vector includes the nptII neomycin phosphotransferase gene, which confers resistance to neomycin and kanamycin (Beck et al., 1982).

The T7 plasmid vector may further comprise transcriptional terminators between the vector backbone and the target gene to prevent read-through transcription from the vector backbone, or may contain other elements as necessary (see U.S. Pat. No. 6,709,861 to Mead and Godiska).

The T7 plasmid vector preferably comprises fewer than about 4000, fewer than about 3000, or fewer than about 2500 base pairs in the absence of an inserted recombinant gene. Increased expression of lac repressor protein resulting from the engineered lacI allele separately maintained in the host strain described herein provides a sufficient amount of lac repressor protein for control of T7 RNA polymerase and target gene expression in the absence of additional copies of the lacI gene. Thus, in a preferred version of the invention, the T7 plasmid vector does not carry a copy of the lacI gene. The absence of a lacI gene on the T7 plasmid vector allows the vector to be reduced by about 1.2 kb. The resulting streamlined cloning vector facilitates biochemical manipulations of DNA in vitro. Because PCR-based manipulations tend to lose fidelity as the size of the amplicon increase, the relatively small size of the vector in the present system lends itself to PCR-based cloning procedures.

The T7 plasmid vector is preferably structured to be a low-copy number vector. "Low-copy number" refers to plasmid copy numbers fewer than about 300 copies of the plasmid within a cell, including less than about 200 copies, 50 copies, 25 copies, 10 copies, or 5 copies. Plasmids containing the ColE1 origin of replication are maintained at a low copy number (~20-40 copies per cell) when the rop gene is present on the plasmid. Plasmids containing the ColE1 original of replication are maintained at about several hundred copies in the absence of the rop gene.

The invention includes variants of any of the sequences disclosed herein.

Variants of the sequences described herein include homologs. Homologs can be identified by homologous nucleic acid and polypeptide sequence analyses. Known nucleic acid and polypeptide sequences in one organism can be used to identify homologous polypeptides in another organism. For example, performing a query on a database of nucleic acid or polypeptide sequences can identify homologs thereof. Homologous sequence analysis can involve BLAST or PSI-BLAST analysis of databases using known polypeptide amino acid sequences (see, e.g., Altschul et al., 1990). Those proteins in the database that have greater than 35% sequence identity are candidates for further evaluation for suitability in the systems and methods of the invention. If desired, manual inspection of such candidates can be carried out in order to narrow the number of candidates that can be further evaluated. Manual inspection is performed by selecting those candidates that appear to have conserved domains. Determining nucleic acid sequences from discovered homologous amino acid sequences or amino acid sequences from discovered homologous nucleic acid sequences can be deduced using the genetic code.

Variants of the coding sequences described herein include degenerate variant sequences that encode the same polypeptides as disclosed herein. Such degenerate variants can be deduced with the genetic code.

Variants of the sequences described herein also include conservative amino acid substitutions of the sequences described herein. A "conservative substitution" means the replacement of one amino acid by an amino acid having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Variants of the sequences described herein include fragments of the sequences described herein. "Fragment" means a portion of the full length sequence. For example, a fragment of a given polypeptide is at least one amino acid fewer in length than the full length polypeptide (e.g. one or more internal or terminal amino acid deletions from either amino or carboxy-termini). Fragments therefore can be any length up to, but not including, the full length polypeptide. Suitable fragments of the polypeptides described herein include but are not limited to those having 50%, 60%, 70%, 75%, 80%, 85%, 90%, 95%, 96%, 97%, 98%, or more of the length of the full length polypeptide.

Variants of the sequences described herein also include repeating units of the sequences described herein. "Repeating units" means a repetition of a given sequence in tandem. Also included are polypeptides having repeating units of fragments of the sequences described herein.

The variant sequences include sequences with about 50%, 60%, 70%, 75%, 80%, 85%, 90%, 95%, 96%, 97%, 98%, or more identity to the sequences described herein. The term "identity" and grammatical variations thereof, mean that two or more referenced entities are the same. Thus, where two protein sequences are identical, they have the same sequence. The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., 1990) has exemplary search parameters as follows: Mismatch −2; gap open 5; gap extension 2. For polypeptide sequence comparisons, a BLASTP algorithm is typically used in combination with a scoring matrix, such as PAM100, PAM 250, and BLOSUM 62.

Suitable variants of the nucleic acid or polypeptide sequences disclosed herein have the same type of activity (without regard to the degree of the activity) as the nucleic acid or polypeptide to which the sequence corresponds. Such activities may be tested according to the assays described in the Examples below and according to methods known in the art.

In addition to providing the aforementioned system, the invention also provides methods of using the system.

One method includes a method of ligase-free cloning of a recombinant gene. The method includes the steps of linearizing a plasmid vector and a target gene into a linearized plasmid and a linearized target gene, respectively, and transforming the mixture into a host. In the context of the methods described herein, "target gene" comprises any component of the genes described herein, including a coding sequence, a promoter, operators, enchancers, etc., either alone or in various combinations. Thus, "linearized target gene" may refer to a linearized promoter, operator, and coding sequence as individual linearized nucleic acid molecules. Alternatively, "linearized target gene" may refer to a linearized promoter, operator, and coding sequence together on one nucleic acid molecule. Similarly, "linearized plasmid" may include several individual fragments which together comprise the plasmid.

The step of linearizing a plasmid and a target gene into a linearized plasmid and a linearized target gene can occur by several methods. In one method of linearization, the plasmid and/or the target gene is linearized with restriction enzymes. With respect to the plasmid, the linearization typically occurs after the plasmid has been amplified by growth of a host harboring the plasmid followed by purification of the amplified plasmid. With respect to the target gene, the linearization typically occurs by enzymatically digesting a cDNA encoding the target gene. In another method of linearization, the plasmid and/or target gene is amplified by PCR. See Sambrook et al. (1989) for a discussion of the procedures relating to restriction digestion and PCR. For insertion of the target gene in the plasmid, it is preferred that that plasmid is linearized within the target gene insertion site.

"Transforming" refers to any method used to cause the uptake of DNA by living cells. The invention includes any known method of introducing DNA into living cells known or hereafter discovered. Various methods include chemical transformation (e.g., calcium chloride-mediated transformation), electroporation, sonication, macroinjection, microinjection, and viral infection. See Sambrook et al., eds., *Molecular Cloning: A Laboratory Manual*, Cold Spring Harbor Lab Publ., 11.51, (1989) for various transformation methods.

Once the linearized plasmid and linearized target gene are introduced within the host, the host's internal machinery produces a recombinant DNA molecular comprising the plasmid and the target gene.

Figure 6:
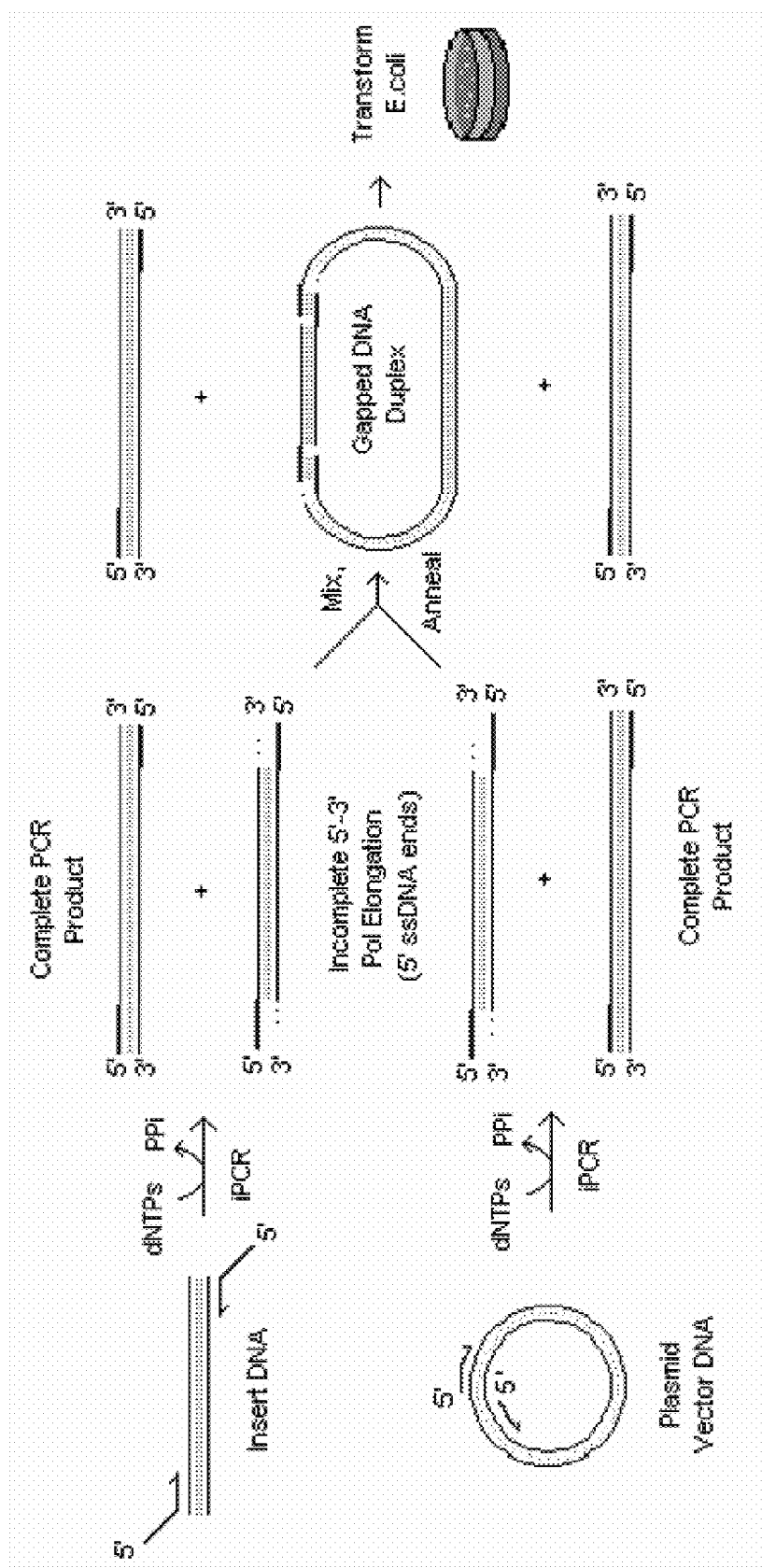
FIG. 6 depicts a ligase-free method of gene cloning using incomplete PCR (iPCR).

A specific method of carrying out ligase-free cloning includes incomplete PCR (iPCR). In iPCR, the 5'→3' polymerase-catalyzed extension of a template is unfinished, so that 5' single-stranded DNA ends remain available for base-pairing. Methods of performing iPCR are described in Li and Elledge, 2007, and U.S. Pub. No. 2007/0292954 to Elledge. A schematic for iPCR and cloning therewith is depicted in FIG. 6. If a plasmid vector is small enough to be efficiently PCR-amplified (<5,000 bp long), as with the T7 plasmid vectors described herein, it can be converted into a linear DNA molecule with 5' single-stranded ends by iPCR. Incomplete 5'→3' elongation during PCR amplification results in a substantial portion of linearized plasmid molecules which contain 15- to 100-nt 5' single-stranded DNA ends. Target genes are iPCR-amplified using 5' tagged primers which contain ~20 nt vector sequences (marked in bold in FIG. 6; see forward and reverse His6 primers in SEQ ID NO:7). One way of introducing complementarity between the iPCR-amplified plasmid and the target gene is to use primers in the plasmid iPCR reaction that have portions complementary to the primers used in the target gene iPCR reaction. iPCR-amplified target gene and plasmid DNAs, which contain complementary 5' single-stranded overhangs, are mixed together, and the resulting gapped DNA duplexes are transformed into the host. This is followed by selection on nutrient plates with an appropriate antibiotic.

Another method of carrying out ligase-free cloning includes in vivo homologous recombination. See Bubeck et al., 1993. This method exploits the natural intracellular enzymatic machinery in the host to produce recombinant DNA molecules. In the method, the plasmid and the target gene are amplified with primers in complete PCR that result in blunt-ended terminal ends of the plasmid having homologous overlap with blunt-ended terminal ends of the target gene.

Homologous overlap from about 5 bp to about 42 and greater is acceptable. Homologous overlap of about 10 bp is preferred. The linearized plasmid and linearized target gene with homologous terminal ends are cotransformed into the host. Maximum yields are obtained with about equimolar concentrations of linearized plasmid and linearized target gene. In some cases, only the target gene must be linearized, such as when a circular plasmid contains homologous regions with a distance spanning the homologous regions that is similar to the length of the target gene.

Other methods of ligase-free cloning are described in Aslanidis and de Jong, 1990; Kuijper et al., 1992; Oliner et al., 1993; and Klock et al., 2008.

The removal of the lacI gene from the plasmid described herein and the resulting reduction in plasmid size render the plasmid described herein particularly suited for ligase-free cloning using the PCR-based methods described above.

Methods of using the system described herein also include expressing either a target gene using the same host used for cloning. The method includes inducing expression of the target gene in the host. The ability to clone DNA and express protein therefrom in the same host is achieved by the tight, inducible control of the target gene in the present system, wherein expression of the target protein (potentially a toxic protein) is substantially prevented or minimized prior to induction, and wherein induction is sufficient to induce a substantial increase in expression of the target gene.

One method of induction includes the direct addition of an inducer to cell media that is either not sufficiently produced by the cell itself or is not produced by the cell at all. Such inducers that may be added to the cell media to induce target gene expression include but are not limited to allolactose, isopropylthiogalactoside (IPTG), methyl-β-D-thiogalactoside, phenyl-β-D-galactose, and ortho-Nitrophenyl-β-galactoside (ONPG). The inducers are preferably added to the cells after growth to mid-log phase at concentrations of about 0.5 mM to 1.0 mM. Other concentrations may be used.

Other methods of induction rely on processes within the host under specific conditions to generate the inducer as an internally produced metabolite. This type of induction is referred to herein as "auto-induction."

The auto-induction method of inducing gene expression in conventional T7 systems has been used for production of recombinant proteins in *E. coli* (Studier, 2005; U.S. Pat. No. 7,560,264 to Studier). Auto-induction of transcription of cloned DNA in cultures of bacterial cells is an approach that employs different carbon sources to support cell growth and protein expression without the requirement to monitor the culture growth state. Auto-induction arises from a complex set of changes in growth conditions and host regulatory responses.

Auto-induction protocols were originally formulated for T7 promoter-based expression, and are based on the function of lac operon regulatory elements in mixtures of glucose, glycerol, and lactose under diauxic growth conditions. During the initial growth period, glucose is preferentially used as a carbon source and protein expression is low due to catabolite repression of alternative carbon utilization pathways and binding interactions between lac repressors and lac operators. As glucose is depleted, catabolite repression is relieved, leading to a shift in cellular metabolism toward the import and consumption of lactose and glycerol. Lactose import results in the production of allolactose from lactose by a reaction of β-galactosidase. Allolactose then acts as the physiological inducer.

An inducible T7 expression system is highly effective and is used for production of proteins from cloned coding sequences in *E. coli*. Although IPTG has typically been used to induce expression of target proteins in the inducible T7 expression system, lactose will also cause induction through auto-induction and, being much cheaper than IPTG, may be preferable for large-scale production (Hoffman et al., 1995).

Methods for carrying out auto-induction in the present system can be performed as described in Studier, 2005; U.S. Pat. No. 7,560,264 to Studier; Blommel et al., 2007; and U.S. Pub. No. 2008/0286749 to Fox et al.

Blommel et al. provide evidence that increasing lacI expression is detrimental to target protein production in inducible systems. Blommel et al. show that increasing expression of lac repressor protein by employing the $lacI^q$ allele in a T5-lac expression system significantly reduced protein expression through auto-induction. Conversely, Blommel et al. also show that manipulation of the lacI promoter to decrease expression of lac repressor protein lead to increased target protein expression through auto-induction. Blommel et al. additionally show that auto-induction using the T7-lac system resulted in even lower target protein expression levels than with the T5-lac system. These teachings suggest that manipulating the lacI promoter to increase lac repressor protein expression, especially in the T7-lac system, would further reduce target protein expression through auto-induction.

The T7-based system described herein produces the unexpected result that the various modifications engineered into the lacI gene in the T7 system of the present invention results not only in extremely low background expression levels but in a significant increase in target expression upon auto-induction. These modifications include placing the lacI coding sequence under the control of a stronger promoter, i.e., $lacI^{q1}$ allele, adding a translational enhancer, and employing an ATG start codon. Without being limited by mechanism, it is believed that the low background expression levels and increase in target expression upon auto-induction is achieved by the system's particular balance among the amount of lac repressor protein produced in the system, the number of available lac operators available for binding, and the amount of inducer produced upon auto-induction. The distances between the various genetic elements on the nucleic acid also play a role in the amount of lac inhibitor produced in the current system to achieve the particular balance.

Thus, the amount of the lac repressor protein expressed in the current system is sufficiently high to substantially inhibit background expression of the recombinant gene when uninduced but sufficiently low to permit induction by auto-induction. The amount of lac repressor protein in the cells preferably permits an increase in expression of the recombinant gene of at least about 10 fold, 100 fold, 200 fold, 300 fold, 400 fold, 500 fold, 600 fold or more upon auto-induction.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The methods, compounds, and compositions of the present invention can comprise, consist of, or consist essentially of the essential elements and limitations described herein, as well as any additional or optional steps, ingredients, components, or limitations described herein or otherwise useful in biochemistry, enzymology and/or genetic engineering.

It is understood that the invention is not confined to the particular construction and arrangement of parts herein illustrated and described, but embraces such modified forms thereof as come within the scope of the following claims.

EXAMPLES

Example 1

Construction of a New lacI Allele for High-Level Expression of lac Repressor Protein in *E. coli*

The chromosomal wild-type lacI gene is transcribed from a promoter characterized by a weak −35 element, and is normally expressed at an intracellular concentration of ~10 nM, or 10 molecules/cell of tetrameric repressor protein. A mutant promoter allele, lacI$^{q1}$ (Calos and Miller, 1981; Glascock and Weickert, 1998) contains a deletion of 15 DNA base pairs in the −35 region of the lac promoter. A consensus −35 element replaces the weak −35 element, resulting in 170-fold higher transcription than wild-type lacI, and 17-fold higher than the point mutant promoter, lacI$^q$ (Calos, 1978).

To achieve even higher levels of lac repressor protein, a novel allele of lacI was constructed that combines the strong (170-fold↑) lacI$^{q1}$ promoter with two additional features that increase the efficiency of lacI mRNA translation. The first of these elements is a translational enhancer derived from the 5' RNA leader sequence of T7 gene 10. The second feature, designed to increase the translation of lacI mRNA, is the substitution of the non-canonical GTG initiation codon with an ATG codon. The combination of the inclusion of the gene 10 translational enhancer and substitution of ATG for GTG as the initiation codon is expected to further increase the level of repressor protein expression by at least 2- to 4-fold. Finally, the strong transcriptional terminator from the tonB gene of *E. coli* was introduced downstream of the lac repressor coding region to ensure efficient termination and to prevent the high level of transcription from the lacI$^{q1}$ promoter from interfering with other plasmid functions. These features were generated using standard molecular biological techniques. This allele is designated here as lacI$^{q1+En}$ and is illustrated in FIGS. 3 and 4.

When harbored on a BAC plasmid vector or integrated into the *E. coli* chromosome, the lacI$^{q1+En}$ construct is maintained at 1 copy/cell. The level of lac repressor produced from the resulting single-copy construct is expected to be at least 300-fold higher than the amount produced from wild-type lacI, or about 30-fold higher than the amount produced by a single-copy of lacI$^q$. This level of repressor is also at least 50% higher than that produced from lacI$^q$ harbored on a multicopy plasmid maintained at ~20 copies/cell.

Example 2

Tight Repression of Target Genes Cloned Under a T7-lac Promoter

A DNA polymerase gene was cloned under the control of the T7-lac promoter in the pET28a vector (Merck, Whitehouse Station, N.J.) and in the pETite vector (Lucigen, Madison, Wis.). The pET28a vector is a ~5.4 kb plasmid having a lac operator adjacent to a T7 promoter and bearing a copy of lacI to provide for increased expression of lac repressor protein. The pETite vector is a ~2.2 kb plasmid with a lac operator adjacent to a T7 promoter but with no lacI gene. The plasmids were transformed into BL21(DE3) cells not harboring lacI$^{q1+En}$ or into BL21(DE3) cells harboring lacI$^{q1+En}$ on a BAC plasmid. Transformants were selected on YT plates containing 30 μg/ml kanamycin. Transformants with the pETite vector could not be obtained in BL21(DE3) cells lacking the lacI$^{q1+En}$ BAC plasmid but were readily obtained in BL21(DE3) cells containing the lacI$^{q1+En}$ BAC plasmid. Single colonies of transformants were inoculated into LB+kanamycin and grown at 37° C. until they reached an optical density at 600 nm (OD$_{600}$) of 0.6-0.8. Samples of uninduced cells were harvested by centrifugation. The remainder of the culture was induced by the addition of 1 mM IPTG, and incubation was continued for an additional 3 hours. Induced cells were harvested as above, and both uninduced and induced cell samples were lysed by heating to 95° C. in SDS gel loading buffer. Equivalent samples (0.05 OD$_{600}$ units) were separated by electrophoresis on a 4-20% denaturing gel and stained with Coomassie blue.

Figure 7:
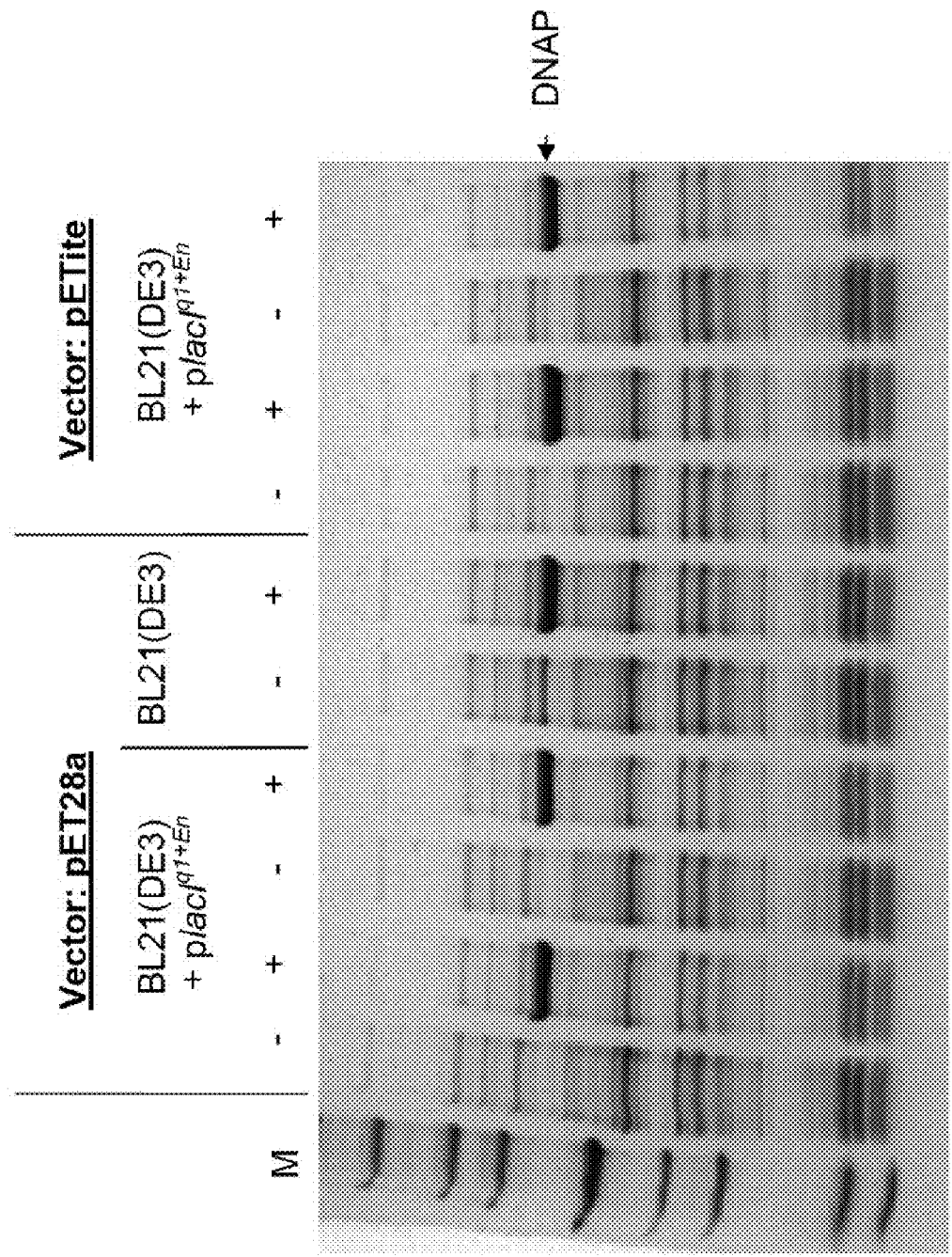
FIG. 7 depicts a gel comparing regulation of target protein expression (DNAP) with various vectors in hosts with and without the lacI$^{qI+En}$ allele under uninduced and induced conditions.

The results are shown in FIG. 7. The lane marked M contains molecular weight markers. Lanes marked − and + contain uninduced (−IPTG) and induced (+IPTG) samples, respectively. The uninduced sample from pET28a-transformed cells without the lacI$^{q1+En}$ allele showed significant accumulation of the DNA polymerase. By contrast, uninduced samples from pET28a- or pETite-transformed cells containing the lacI$^{q1+En}$ allele (BL21(DE3)+placI$^{q1+En}$) showed very low background levels of expression. Upon treatment with 1 mM IPTG for 3 hours, all samples were induced to express high levels of the DNA polymerase (FIG. 7). However, the samples containing the lacI both within the host and on the vector, i.e., pET28a-transformed cells containing the lacI$^{q1+En}$ allele (BL21(DE3)+placI$^{q1+En}$), showed slightly lower expression upon induction.

Despite the having a lac operator adjacent to the T7 promoter and an additional copy of the lacI gene, pET series vectors such as in the pET28a vector allow leaky expression of target proteins in the uninduced state. An example of such leaky expression is shown in FIG. 7. Improved control of this leaky expression has been achieved by incorporating the overexpressing lac repressor allele, lacI$^{q1+En}$, in the BL21(DE3) host strain on a single-copy BAC plasmid. The level of lac repressor protein produced from the lacI$^{q1+En}$ allele harbored on a BAC plasmid in BL21(DE3) cells was sufficient to allow elimination of lacI from the T7 expression vector while still achieving low background levels under uninduced conditions (FIG. 7). In addition, further removing the lacI gene from the vector provided for the highest dynamic range of expression between uninduced and induced conditions (FIG. 7).

Example 3

Expression of a Fluorescent Protein in BL21(DE3) Harboring lacI$^{q1+En}$ Upon IPTG Induction A gene encoding a yellow fluorescent protein was cloned under the control of a T7-lac promoter in the pET28a vector, which harbors a copy of lacI. The plasmid was transformed into four different T7 host strains and expression of the fluorescent protein after induction with IPTG was evaluated. The strains tested were BL21(DE3) with no additional lacI, BL21(DE3) harboring lacI$^{q1+En}$, NEB T7 Express (New England BioLabs, Ipswich, Mass.) harboring lacI$^q$ on a single copy mini F plasmid, and NEB T7 Express harboring both lacI$^q$ and lysY. The lysY gene encodes a variant form of T7 lysozyme, an inhibitor of T7 RNA polymerase (WO 2008/073746 to Samuelson et al. and Cheng et al., 1994). Transformants were inoculated into LB+kanamycin and grown at 37° C. until they reached an OD$_{600}$ of 0.6-0.8. Samples of uninduced cells were harvested by centrifugation, and the remainder of the culture was induced by the addition of 1 mM IPTG. Induced samples were harvested after 1 hour and 3 hours of induction at 37° C. Uninduced and induced cells were resuspended in water, and samples (200 µl) containing equivalent OD$_{600}$ units were analyzed on a fluorescence plate reader with excitation at 428 nm and emission detected at 528 nm. Aliquots of the samples were also analyzed by electrophoresis on a 4-20% denaturing gel and staining with Coomassie blue.

Figure 8A:
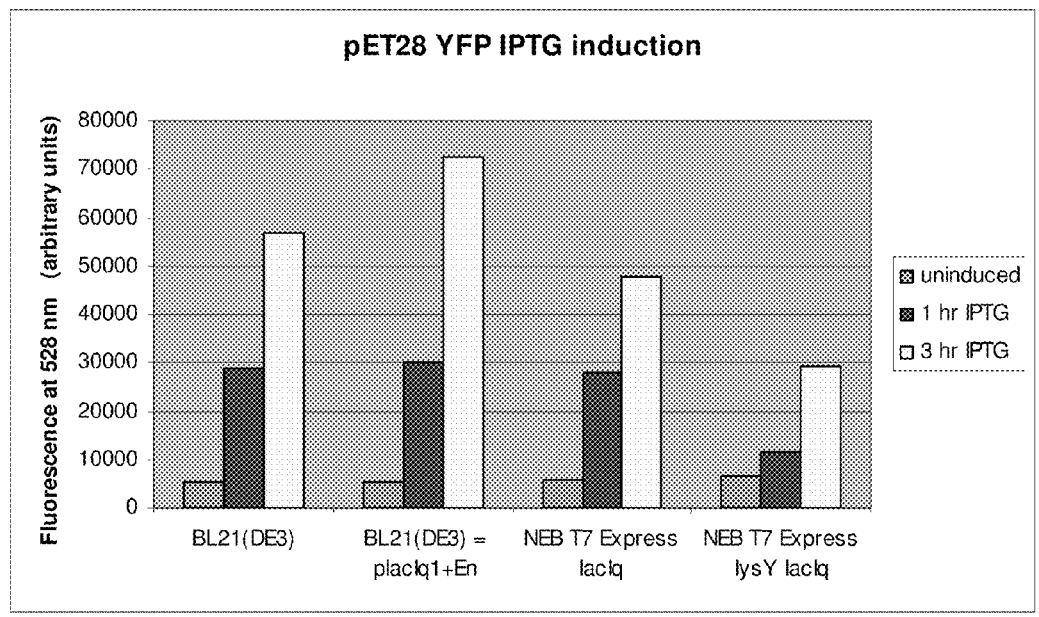
FIG. 8A depicts relative fluorescence from samples from uninduced and IPTG-induced T7 host strains harboring yellow fluorescent protein under control of a T7-lac promoter and also harboring various lacI alleles, including the lacI$^{qI+En}$ allele.
Figure 8B:
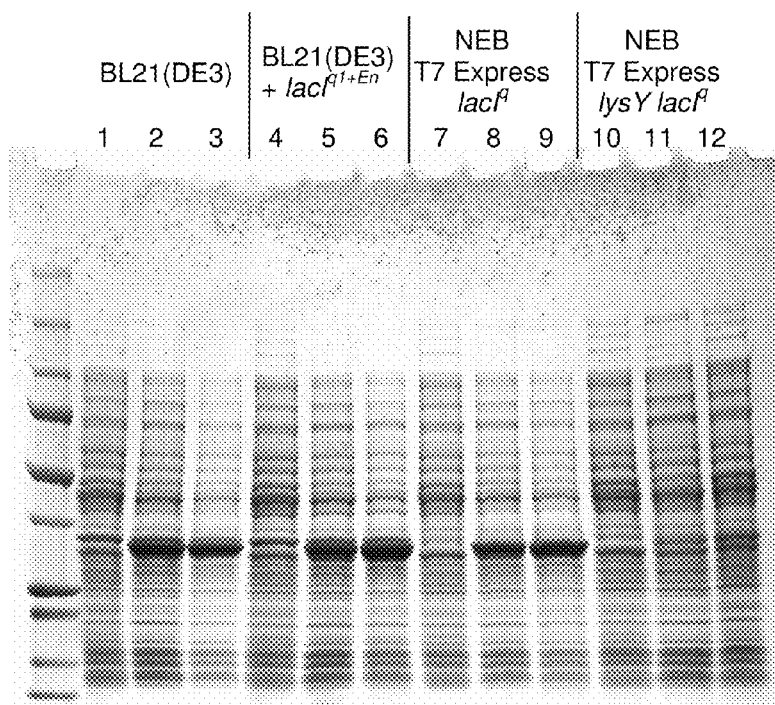
FIG. 8B depicts a Coomassie blue-stained gel of the samples from FIG. 8A.

Results are shown in FIGS. 8A and 8B. FIG. 8A shows the relative fluorescence of uninduced and induced samples of the four host strains. The BL21(DE3) cells with or without lacI$^{q1+En}$ and the NEB T7 Express lacI$^q$ cells all produced similar levels of fluorescence after induction for 1 hour. After 3 hours of induction, the BL21(DE3) cells harboring lacI$^{q1+En}$ showed slightly higher fluorescence than the standard BL21(DE3) and NEB T7 Express lacI$^q$ cells. The NEB T7 Express lacI$^q$ lysY cells developed fluorescence at a much slower rate, with significantly less fluorescence than the other 3 strains at both 1 hour and 3 hours of induction. FIG. 8B shows the Coomassie blue-stained denaturing polyacrylamide gel, with lanes 1, 4, 7, and 10 showing uninduced samples; lanes 2, 5, 8, and 11 showing samples induced for 1 hr; and lanes 3, 6, 9, and 12 showing samples induced for 3 hrs. FIG. 8 B confirms the similar yields of induced protein in all but the NEB T7 Express lacI$^q$ lysY cells, which produced significantly less of the induced protein. Thus, the high level of lac repressor expression in BL21(DE3) cells harboring lacI$^{q1+En}$ does not interfere with rapid, high-level expression of a gene under the control of a T7-lac promoter.

Example 4

Enhanced Expression of a Fluorescent Protein in BL21(DE3) Harboring lacI$^{q1+En}$ During Auto-Induction The T7 host strains described in Example 3 harboring the yellow fluorescent protein gene cloned into pET28a were also subjected to auto-induction. Colonies were inoculated into LB medium containing kanamycin and supplemented with "OVERNIGHT EXPRESS"-brand auto-induction solutions (Novagen, EMD, Darmstadt, Germany) as recommended by the manufacturer. Cultures were grown at 37° C. for 16 hours, and samples containing equivalent OD$_{600}$ units were harvested by centrifugation. Cells were resuspended in water, and fluorescent protein expression was quantitated using a fluorescence plate reader as described above.

Figure 9:
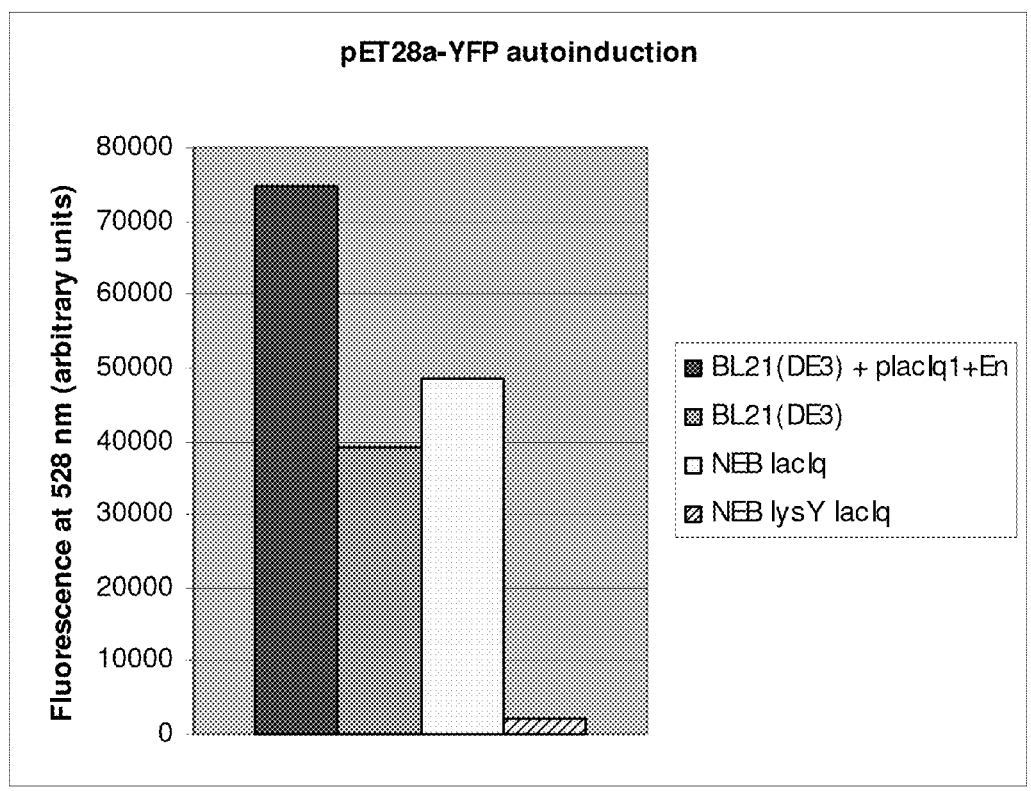
FIG. 9 depicts relative fluorescence from samples from auto-induced T7 host strains harboring yellow fluorescent protein under the control of a T7-lac promoter and also harboring various lacI alleles, including the lacI$^{qI+En}$ allele.

The results are shown in FIG. 9. The BL21(DE3) strain without lacI$^{q1+En}$ and the NEB T7 Express lacI$^q$ strains produced comparable levels of fluorescence, while the NEB T7 Express lacI$^q$ lysY strain failed to develop fluorescence. Surprisingly, the BL21(DE3) cells harboring lacI$^{q1+En}$ allele exhibited approximately 2-fold more fluorescence than the BL21(DE3) strain without lacI$^{q1+En}$ or the NEB T7 Express lacI$^q$ strain.

The increase in target protein expression upon auto-induction in strains harboring the lacI$^{q1+En}$ allele compared to strains harboring the lacI$^q$ allele or the wild-type lacI allele was unexpected, and is contrary to results obtained with a lac-regulated promoter derived from bacteriophage T5 (Blommel et al., 2007 Biotechnol. Prog. 23: 585-598). Blommel et al. found a negative correlation between the dosage of lac repressor protein and the yield of target fluorescent protein during auto-induction. The presence of a lacI$^q$ allele on the T5 promoter expression plasmid severely reduced the expression of a target fluorescent protein in comparison to a plasmid-harbored wild-type lacI allele.

Thus, the lacI$^{q1+En}$ allele and/or the expression system taught herein are exceptionally suited for the auto-induction method of inducing target protein expression.

REFERENCES CITED

U.S. Patent Documents

U.S. Pat. No. 4,952,496 August 1990 Studier et al. "Cloning and expression of the gene for bacteriophage T7 RNA polymerase"

U.S. Pat. No. 5,693,489 December 1997 Studier et al. "Cloning and expression of the gene for bacteriophage T7 RNA polymerase"

U.S. Pat. No. 5,693,489 November 1998 Studier and Dubendorff "Cloning and expression of autogenes encoding RNA polymerases of T7-like bacteriophages"

U.S. Pat. No. 5,869,320 February 1999 Studier et al. "Cloning and expression of the gene for bacteriophage T7 RNA polymerase"

U.S. Pat. No. 6,709,861 March 2004 Mead and Godiska "Cloning Vectors and Vector Components"

U.S. Pat. No. 6,569,669 May 2003 Raleigh "Host strain for low uninduced expression of foreign RNA polymerase genes"

U.S. Pat. No. 7,560,264 July 2009 Studier "High density growth of T7 expression strains with auto-induction option"

U.S. Patent Applications

U.S. Pub. No. 20070292954 December 2007 Elledge "Generation of recombinant DNA by sequence- and ligation-independent cloning"

U.S. Pub. No. 20080286749 November 2008 Fox et al. "Enhanced protein expression using auto-induction media"

International Applications

WO 2008/073746 June 2008 Samuelson et al.

Other References

Altschul S F, Gish W, Miller W, Myers E W, and Lipman D J (1990) "Basic local alignment search tool." J. Mol. Biol. 215(3): 403-10

Angrand P O, Daigle N, van der Hoeven F, Schöler H R, and Stewart A F (1999) "Simplified generation of targeting constructs using ET recombination." *Nucleic Acids Res.* 27(17):e16.

Aslanidis C and de Jong P J (1990) "Ligation-independent cloning of PCR products (LIC-PCR).: *Nucleic Acids Res.* 18: 6069-6074.

Beck E, Ludwig G, Auerswald E A, Reiss B, and Schaller H (1982) "Nucleotide sequence and exact localization of the neomycin phosphotransferase gene from transposon Tn5." *Gene* 19: 327-336.

Blommel P G, Becker K J, Duvnjak P, and Fox B G (2007) "Enhanced bacterial protein expression during auto-induction obtained by alteration of lac repressor dosage and medium composition." *Biotechnol. Prog.* 23(3): 585-598.

Blow N (2008) "Structural genomics: inside a protein structure initiative center." *Nature Methods* 5: 203-207.

Bolivar F, Rodriguez R L, Greene P J, Betlach M C, Heyneker H L, and Boyer H W (1977) "Construction and characterization of new cloning vehicles. II. A multi-purpose cloning system." *Gene* 2: 95-113.

Bubeck P, Winkler M, and Bautsch W (1993) "Rapid cloning by homologous recombination in vivo." *Nucleic Acids Res.* 21(15): 3601-3602.

Calos M P (1978) "DNA sequence for a low-level promoter of the lac repressor and an 'up' promoter mutation." *Nature* 274: 762-765.

Calos M P and Miller J H (1981) "The DNA sequence change resulting from the IQ1 mutation, which greatly increases promoter strength." *Molecular & general genetics* 183: 559-560.

Chandonia J M and Brenner S E (2006) "The impact of structural genomics: expectations and outcomes." *Science* 311: 347-351.

Chen E (1994) "Host strain selection for bacterial expression of toxic proteins." *Methods in Enzymology* 241: 29-46.

Cheng X, Zhang X, Pflugrath J W, and Studier F W (1994) "The Structure of bacteriophage T7 lysozyme, a zinc amidase and an inhibitor of T7 RNA polymerase." *Proc. Natl. Acad. Sci.* USA 91:4034-4038.

Cohen S N, Chang A C, Boyer H W, and Helling R B (1973) "Construction of biologically functional bacterial plasmids in vitro." *Proc. Natl. Acad. Sci.* USA 70: 3240-3244.

Davanloo P, Rosenberg A H, Dunn J J, and Studier F W (1984) "Cloning and expression of the gene for bacteriophage T7 RNA polymerase." *Proc. Natl. Acad. Sci.* USA 81: 2035-2039.

Denhardt D T and Colasanti J (1988) "A survey of vectors for regulating expression of cloned DNA in *E. coli.*" *Biotechnology* 10: 179-203.

Dubendorff J W and Studier F W (1991) "Controlling basal expression in an inducible expression system by blocking the target T7 promoter with lac repressor." *J. Mol. Biol.* 219: 45-59.

Glascock C B and Weickert M J (1998) "Using chromosomal lacIQ1 to control expression of genes on high copy-number plasmids in *Escherichia coli.*" *Gene* 223: 221-231.

Godiska R, Patterson M, Schoenfeld T, and Mead D A (2005) "Beyond pUC: Vectors for Cloning Unstable DNA." In: Kieleczawa J, ed., *DNA Sequencing: Optimizing the Process and Analysis,* 1st edition. Jones and Bartlett Publishers, Inc., Sudbury, Mass., pp. 55-76.

Hoffman B J, Broadwater J A, Johnson P, Harper J, Fox G B, and Kenealy W R (1995) "Lactose fed-batch overexpression of recombinant metalloproteins in *Escherichia coli.* BL21(DE3): Process control yielding high levels of metal incorporated, soluble protein." *Protein Expr. Purif.* 6: 646-654.

Klock H E, Koesema E J, Knuth M W, and Lesley S A (2008) "Combining the polymerase incomplete primer extension method for cloning and mutagenesis with microsequencing to accelerate structural genomics efforts." *Proteins* 71: 982-994.

Kuijper J L, Wiren K M, Mathies L D, Gray C L, and Hagen F S (1992) "Functional cloning vectors for use in directional cDNA cloning using cohesive ends produced with T4 DNA polymerase." *Gene* 112: 147-155.

Lehmeier B and Amann E (1992) "Tac promoter vectors incorporating the bacteriophage gene 10 translational enhancer sequence for improved expression of cloned genes in *Escherichia coli.*" *J Biotechnol.* 23: 153-165.

Li M Z and Elledge S J (2007) "Harnessing homologous recombination in vitro to generate recombinant DNA via SLIC." *Nature Methods* 4: 251-256.

Lin-Chao S, Chen W T, and Wong T T (1992) "High copy number of the pUC plasmid results from a Rom/Rop suppressible point mutation in RNAII." *Molecular Microbiology* 6: 3385-3393.

MacFerrin K D, Terranova M P, Schreiber S L, and Verdine G L (1990) "Overproduction and dissection of proteins by the expression-cassette polymerase chain reaction." *Proc. Natl. Acad. Sci.* USA 87: 1937-1941.

Miroux, B and Walker, J E (1996) "Over-production of proteins in *Escherichia coli*: mutant hosts that allow synthesis of some membrane proteins and globular proteins." *J Mol. Biol.* 260: 289-298.

Oliner J D, Kinzer K W, and Vogelstein B (1993) "In vivo cloning of PCR products in *E. coli.*" *Nucleic Acids Res.* 21: 5192-5197.

Olins P O, Devine C S, Rangwala S H, and Kavka K S. (1988) "The T7 gene 10 leader RNA, a ribosome-binding site that dramatically enhances the expression of foreign genes in *Escherichia coli.*" *Gene* 73: 227-235.

Olins P O, Rangwala S H (1989) "A novel sequence element derived from bacteriophage T7 mRNA acts as an enhancer of translation of the lacZ gene in *Escherichia coli.*" *J Biol Chem.* 264: 16973-16976.

Payne C M, Mullins L J and Mullins J J (1999) "Manipulating large genomic clones via in vivo recombination in bacteria." *J. Hum. Hypertens.* 13(12): 845-8

Peranen J, Rikkonen M, Hyvonen M, and Kaariainen L (1996) "T7 vectors with modified T7lac promoter for expression of proteins in *Escherichia coli.*" *Anal Biochem.* 236:371-373.

Posfai G, Koob M D, Kirkpatrick H A and Blattner F R (1997) "Versatile insertion plasmids for targeted genome manipulations in bacteria: isolation, deletion, and rescue of the pathogenicity island LEE of the *Escherichia coli* O157:H7 genome." *J. Bacteriol.* 179: 4426-28.

Roge J and Betton J M (2005) "Use of pIVEX plasmids for protein overproduction in *Escherichia coli.*" *Microbial Cell Factories* 4:18.

Rong M, Biao H, McAllister W T, and Durbin R K (1998) "Promoter specificity determinants of T7 RNA polymerase." *Proc. Natl. Acad. Sci.* USA 95: 515-519.

Rosenberg A H, Lade B N, Chui D S, Lin S W, Dunn J J, and Studier F W (1987) "Vectors for selective expression of cloned DNAs by T7 RNA polymerase." *Gene* 56: 125-135.

Saiki R, Scharf S, Faloona F, Mullis K, Horn G, and Erlich H (1985). "Enzymatic amplification of beta-globin genomic sequences and restriction site analysis for diagnosis of sickle cell anemia." *Science* 230: 1350-1354.

Sambrook et al., eds. (1989) *Molecular Cloning: A Laboratory Manual*, Cold Spring Harbor Lab Publ., 11.51

Studier F W (2005) "Protein production by auto-induction in high density shaking cultures." *Protein Expression & Purification* 41: 207-234.

Studier F W and Moffatt B A (1986) "Use of bacteriophage T7 RNA polymerase to direct selective high-level expression of cloned genes." *J. Mol. Biol.* 189: 113-130.

Studier F W, Rosenberg A H, Dunn J J, and Dubendorff J W (1990) "Use of T7 RNA polymerase to direct expression of cloned genes." Methods in Enzymology 185: 60-89.

Summers D (1998) "Timing, self-control and a sense of direction are the secrets of multicopy plasmid stability." *Molecular Microbiology* 29: 1137-1145.

Walhout A J, Temple G F, Brasch M A, Hartley J L, Lorson M A, van den Heuvel S, and Vidal M (2000) "GATEWAY recombinational cloning: application to the cloning of large numbers of open reading frames or ORFeomes." *Methods in Enzymology* 328: 575-592.

Yannisch-Perron C, Vieira J, and Messing J (1985) "Improved M13 phage cloning vectors and host strains: nucleotide sequences of the M13mp18 and pUC19 vectors." *Gene* 33: 103-119.

We claim:

1. A system for cloning and/or expressing a target gene comprising:
   a host comprising:
      a T7 RNA polymerase gene configured to produce a T7 RNA polymerase protein, the T7 RNA polymerase gene including:
         a T7 RNA polymerase coding sequence;
         a first promoter operationally linked to the T7 RNA polymerase coding sequence; and
         a first lac operator operationally linked to the promoter;
      a single copy of a lacI gene configured to produce an amount of lac repressor protein including:
         a lacI coding sequence;
         a second promoter operationally linked to the lacI coding sequence, wherein the second promoter comprises nucleotides 1-56 of SEQ ID NO:4; and
         a translational enhancer sequence comprising a sequence at least about 90% identical to nucleotides 62-71 of SEQ ID NO:4 or comprising a sequence selected from the group consisting of TTAACTTTA, TTAACTT, TTAACT, ACTTTA, AATTTTA, GGCTTT, AACTTTG, AACTTT, and TAACTTTA; and
   a T7 plasmid vector for transforming into the host comprising:
      a target gene insertion site;
      a T7 promoter operationally linked to the target gene insertion site; and
      a second lac operator operationally linked to the T7 promoter, wherein the T7 plasmid vector is devoid of a gene for expressing lac repressor;
   wherein the amount of lac repressor protein inhibits expression of the target gene in the absence of inducer and permits at least a 10-fold increase in expression of the target gene in the presence of inducer.

2. The system of claim 1 wherein the T7 RNA polymerase coding sequence is T7 gene 1.

3. The system of claim 1 wherein the first promoter and the first lac operator together comprise SEQ ID NO:1.

4. The system of claim 1 wherein the lacI coding sequence comprises an ATG initiation codon.

5. The system of claim 1 wherein the translational enhancer sequence comprises nucleotides 62-71 of SEQ ID NO:4.

6. The system of claim 1 wherein the lacI gene further comprises a transcriptional terminator having nucleotides 1170-1208 of SEQ ID NO:4.

7. The system of claim 1 wherein the lacI gene produces at least 300-fold higher levels of lac repressor protein relative to wild-type lacI.

8. The system of claim 1 wherein the amount of lac repressor protein permits at least a 500-fold increase in expression of the target gene in presence of an amount of inducer generated through auto-induction.

9. The system of claim 1 wherein the lacI gene is about 80% identical to SEQ ID NO:4.

10. The system of claim 1, wherein the T7 plasmid vector contains 3000 or fewer base pairs in the absence of an inserted target gene.

11. A system for cloning and/or expressing a target gene comprising:
   a host including:
      a T7 RNA polymerase gene configured to produce a T7 RNA polymerase protein, the T7 RNA polymerase gene including:
         a T7 RNA coding sequence;
         a first promoter operationally linked to the T7 RNA polymerase coding sequence; and
         a first lac operator operationally linked to the promoter;
      a single copy of a lacI gene configured to produce an amount of lac repressor protein including:
         a lacI coding sequence comprising an ATG initiation codon;
         a second promoter operationally linked to the lacI coding sequence, wherein the second promoter comprises nucleotides 1-56 of SEQ ID NO:4; and
         a translational enhancer sequence, wherein the translational enhancer sequence comprises nucleotides 62-71 of SEQ ID NO:4;
   a T7 plasmid vector for transforming into the host comprising:
      a target gene insertion site;
      a T7 promoter operationally linked to the target gene insertion site; and
      a second lac operator operationally linked to the T7 promoter, wherein the T7 plasmid vector is devoid of a gene for expressing lac repressor, and wherein the T7 plasmid vector contains 3000 or fewer base pairs in the absence of an inserted target gene;
   wherein the amount of lac repressor protein inhibits expression of the target gene in the absence of inducer and permits at least a 10-fold increase in expression of the target gene in the presence of inducer.

12. The system of claim 11 wherein the amount of lac repressor protein permits at least a 10-fold increase in expression of the target gene in presence of an amount of inducer generated through auto-induction.

13. The system of claim 1 wherein the translational enhancer sequence comprises a sequence at least about 90% identical to nucleotides 62-71 of SEQ ID NO:4.

14. The system of claim 1 wherein the translational enhancer sequence comprises a sequence selected from the group consisting of TTAACTTTA, TTAACTT, TTAACT, ACTTTA, AATTTTA, GGCTTT, AACTTTG, AACTTT, and TAACTTTA.

15. A method of ligase-free cloning and/or expressing a target gene with the system as recited in claim 1 comprising:
   linearizing the T7 plasmid vector and the target gene into a linearized plasmid and a linearized target gene and;
   transforming the linearized plasmid and the linearized target gene into the host.

16. The method of claim 15 wherein the linearizing comprises incomplete PCR, wherein the linearized plasmid and the linearized nucleic acid each comprise 5' single-stranded ends.

17. The method of claim 15 wherein the linearizing comprises incorporating homologous terminal ends on the linearized plasmid and the linearized nucleic acid by PCR, the linearized plasmid and the linearized nucleic acid each comprise blunt ends, and wherein the cloning the target gene comprises in vivo homologous recombination in the host.

18. The method of claim 15 further comprising inducing expression of the target gene.

19. The method of claim 18 wherein the inducing comprises adding an inducer selected from the group consisting of allolactose, isopropylthiogalactoside (IPTG), methyl-β-D-thiogalactoside, phenyl-β-D-galactose, and ortho-Nitrophenyl-β-galactoside (ONPG).

20. The method of claim 18 wherein the inducing comprises auto-induction.

21. The method of claim 20 wherein an amount of inducer produced by the auto-induction is sufficient to increase expression of the target gene by at least 500-fold.

\* \* \* \* \*

SEQUENCE LISTING

```
<160> NUMBER OF SEQ ID NOS: 9

<210> SEQ ID NO 1
<211> LENGTH: 43
<212> TYPE: DNA
<213> ORGANISM: Escherichia coli
<220> FEATURE:
<221> NAME/KEY: misc_feature
<222> LOCATION: (22)..(43)
<223> OTHER INFORMATION: lac operator

<400> SEQUENCE: 1
gcttccggct cgtataatgt gtggaattgt gagcggataa caa            43

<210> SEQ ID NO 2
<211> LENGTH: 24
<212> TYPE: DNA
<213> ORGANISM: Escherichia coli

<400> SEQUENCE: 2
tggaattgtg agcggataac aatt                                 24

<210> SEQ ID NO 3
<211> LENGTH: 20
<212> TYPE: DNA
<213> ORGANISM: Escherichia coli

<400> SEQUENCE: 3
taatacgact cactataggg                                      20

<210> SEQ ID NO 4
<211> LENGTH: 1208
<212> TYPE: DNA
<213> ORGANISM: Artificial Sequence
<220> FEATURE:
<223> OTHER INFORMATION: Recombinant gene
<220> FEATURE:
<221> NAME/KEY: promoter
<222> LOCATION: (1)..(56)
<220> FEATURE:
<221> NAME/KEY: enhancer
<222> LOCATION: (62)..(71)
<220> FEATURE:
<221> NAME/KEY: CDS
<222> LOCATION: (87)..(1169)
<220> FEATURE:
<221> NAME/KEY: terminator
<222> LOCATION: (1170)..(1208)

<400> SEQUENCE: 4
agcggcatgc atttacgttg acaccacctt tcgcggtatg gcatgatagc gcccggaagg      60
ttttaactat agtaaggagt ctaagc atg aaa cca gta acg tta tac gat gtc     113
                             Met Lys Pro Val Thr Leu Tyr Asp Val
```

-continued

```
            1                   5
gca gag tat gcc ggt gtc tct tat cag acc gtt tcc cgc gtg gtg aac    161
Ala Glu Tyr Ala Gly Val Ser Tyr Gln Thr Val Ser Arg Val Val Asn
10              15                  20                  25 cag gcc agc cac gtt tct gcg aaa acg cgg gaa aaa gtg gaa gcg gcg    209
Gln Ala Ser His Val Ser Ala Lys Thr Arg Glu Lys Val Glu Ala Ala
            30                  35                  40 atg gcg gag ctg aat tac att ccc aac cgc gtg gca caa caa ctg gcg    257
Met Ala Glu Leu Asn Tyr Ile Pro Asn Arg Val Ala Gln Gln Leu Ala
                45                  50                  55 ggc aaa cag tcg ttg ctg att ggc gtt gcc acc tcc agt ctg gcc ctg    305
Gly Lys Gln Ser Leu Leu Ile Gly Val Ala Thr Ser Ser Leu Ala Leu
            60                  65                  70 cac gcg ccg tcg caa att gtc gcg gcg att aaa tct cgc gcc gat caa    353
His Ala Pro Ser Gln Ile Val Ala Ala Ile Lys Ser Arg Ala Asp Gln
    75                  80                  85 ctg ggt gcc agc gtg gtg gtg tcg atg gta gaa cga agc ggc gtc gaa    401
Leu Gly Ala Ser Val Val Val Ser Met Val Glu Arg Ser Gly Val Glu
90              95                  100                 105 gcc tgt aaa gcg gcg gtg cac aat ctt ctc gcg caa cgc gtc agt ggg    449
Ala Cys Lys Ala Ala Val His Asn Leu Leu Ala Gln Arg Val Ser Gly
                110                 115                 120 ctg atc att aac tat ccg ctg gat gac cag gat gcc att gct gtg gaa    497
Leu Ile Ile Asn Tyr Pro Leu Asp Asp Gln Asp Ala Ile Ala Val Glu
            125                 130                 135 gct gcc tgc act aat gtt ccg gcg tta ttt ctt gat gtc tct gac cag    545
Ala Ala Cys Thr Asn Val Pro Ala Leu Phe Leu Asp Val Ser Asp Gln
        140                 145                 150 aca ccc atc aac agt att att ttc tcc cat gaa gac ggt acg cga ctg    593
Thr Pro Ile Asn Ser Ile Ile Phe Ser His Glu Asp Gly Thr Arg Leu
    155                 160                 165 ggc gtg gag cat ctg gtc gca ttg ggt cac cag caa atc gcg ctg tta    641
Gly Val Glu His Leu Val Ala Leu Gly His Gln Gln Ile Ala Leu Leu
170                 175                 180                 185 gcg ggc cca tta agt tct gtc tcg gcg cgt ctg cgt ctg gct ggc tgg    689
Ala Gly Pro Leu Ser Ser Val Ser Ala Arg Leu Arg Leu Ala Gly Trp
                190                 195                 200 cat aaa tat ctc act cgc aat caa att cag ccg ata gcg gaa cgg gaa    737
His Lys Tyr Leu Thr Arg Asn Gln Ile Gln Pro Ile Ala Glu Arg Glu
            205                 210                 215 ggc gac tgg agt gcc atg tcc ggt ttt caa caa acc atg caa atg ctg    785
Gly Asp Trp Ser Ala Met Ser Gly Phe Gln Gln Thr Met Gln Met Leu
        220                 225                 230 aat gag ggc atc gtt ccc act gcg atg ctg gtt gcc aac gat cag atg    833
Asn Glu Gly Ile Val Pro Thr Ala Met Leu Val Ala Asn Asp Gln Met
    235                 240                 245 gcg ctg ggc gca atg cgc gcc att acc gag tcc ggg ctg cgc gtt ggt    881
Ala Leu Gly Ala Met Arg Ala Ile Thr Glu Ser Gly Leu Arg Val Gly
250                 255                 260                 265 gcg gat atc tcg gta gtg gga tac gat gat acc gaa gac agc tca tgt    929
Ala Asp Ile Ser Val Val Gly Tyr Asp Asp Thr Glu Asp Ser Ser Cys
                270                 275                 280 tat atc ccg ccg tta acc acc atc aaa cag gat ttt cgc ctg ctg ggg    977
Tyr Ile Pro Pro Leu Thr Thr Ile Lys Gln Asp Phe Arg Leu Leu Gly
            285                 290                 295 caa acc agc gtg gac cgc ttg ctg caa ctc tct cag ggc cag gcg gtg   1025
Gln Thr Ser Val Asp Arg Leu Leu Gln Leu Ser Gln Gly Gln Ala Val
        300                 305                 310 aag gac aat cag ctg ttg ccc gtc tca ctg gtg aaa aga aaa acc acc   1073
Lys Asp Asn Gln Leu Leu Pro Val Ser Leu Val Lys Arg Lys Thr Thr
```

```
            315                 320                 325
ctg gcg ccc aat acg caa acc gcc tct ccc cgc gcg ttg gcc gat tca    1121
Leu Ala Pro Asn Thr Gln Thr Ala Ser Pro Arg Ala Leu Ala Asp Ser
330                 335                 340                 345 tta atg cag ctg gca cga cag gtt tcc cga ctg gaa agc ggg cag taa    1169
Leu Met Gln Leu Ala Arg Gln Val Ser Arg Leu Glu Ser Gly Gln
                350                 355                 360 agcagaaagt caaaagcctc cgaccggagg cttttgact                         1208

<210> SEQ ID NO 5
<211> LENGTH: 360
<212> TYPE: PRT
<213> ORGANISM: Artificial Sequence
<220> FEATURE:
<223> OTHER INFORMATION: Synthetic Construct

<400> SEQUENCE: 5

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
                20                  25                  30

Lys Thr Arg Glu Lys Val Glu Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
                100                 105                 110

Asn Leu Leu Ala Gln Arg Val Ser Gly Leu Ile Ile Asn Tyr Pro Leu
            115                 120                 125

Asp Asp Gln Asp Ala Ile Ala Val Glu Ala Ala Cys Thr Asn Val Pro
        130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Asp Asn Gln Leu Leu Pro
```

```
305                 310                 315                 320
Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 6
<211> LENGTH: 56
<212> TYPE: DNA
<213> ORGANISM: Escherichia coli

<400> SEQUENCE: 6
cgttgacacc atcgaatggt gcaaaacctt tcgcggtatg gcatgatagc gcccgg      56

<210> SEQ ID NO 7
<211> LENGTH: 2235
<212> TYPE: DNA
<213> ORGANISM: Artificial Sequence
<220> FEATURE:
<223> OTHER INFORMATION: Plasmid Vector
<220> FEATURE:
<221> NAME/KEY: promoter
<222> LOCATION: (51)..(70)
<223> OTHER INFORMATION: T7 promoter
<220> FEATURE:
<221> NAME/KEY: misc_feature
<222> LOCATION: (71)..(88)
<223> OTHER INFORMATION: lac operator
<220> FEATURE:
<221> NAME/KEY: misc_feature
<222> LOCATION: (101)..(145)
<223> OTHER INFORMATION: Reverse complement of pimer for C-terminal His6
<220> FEATURE:
<221> NAME/KEY: misc_feature
<222> LOCATION: (119)..(163)
<223> OTHER INFORMATION: Reverse complement of pimer for N-terminal His6
<220> FEATURE:
<221> NAME/KEY: misc_feature
<222> LOCATION: (146)..(185)
<223> OTHER INFORMATION: Forward primer for C-terminal His6
<220> FEATURE:
<221> NAME/KEY: misc_feature
<222> LOCATION: (164)..(198)
<223> OTHER INFORMATION: Forward primer for N-terminal His6 tag
<220> FEATURE:
<221> NAME/KEY: misc_feature
<222> LOCATION: (377)..(992)
<223> OTHER INFORMATION: Reverse complement of origin of replication
<220> FEATURE:
<221> NAME/KEY: misc_feature
<222> LOCATION: (1041)..(1232)
<223> OTHER INFORMATION: Reverse complement of ROP gene
<220> FEATURE:
<221> NAME/KEY: misc_feature
<222> LOCATION: (1233)..(2048)
<223> OTHER INFORMATION: Reverse complement of kanamycin resistance gene

<400> SEQUENCE: 7
ggcagtgagc gcaacgcaat taatgtgagt tagctcactc attaggcacc taatacgact      60
cactataggg tgtgagcgga taacaatttc acgtggaaca gctagaaata attttgttta     120
actataagaa ggagatatac atatgcatca tcaccaccat cactaataga gcggccgcca     180
ccgctgagca ataactagca taaccccttg ggcctctaa acgggtcttg aggggttttt      240
tgctgaaagg aggaactata tccgggtaac gaattcaagc ttgatatcat tcaggacgag     300
cctcagactc cagcgtaact ggactgcaat caactcactg gctcaccttc acgggtgggc     360
ctttcttcgg tagaaaatca aaggatcttc ttgagatcct ttttttctgc gcgtaatctg     420
```

-continued

```
ctgcttgcaa acaaaaaaac caccgctacc agcggtggtt tgtttgccgg atcaagagct    480
accaactctt tttccgaggt aactggcttc agcagagcgc agataccaaa tactgttctt    540
ctagtgtagc cgtagttagg ccaccacttc aagaactctg tagcaccgcc tacatacctc    600
gctctgctaa tcctgttacc agtggctgct gccagtggcg ataagtcgtg tcttaccggg    660
ttggactcaa gacgatagtt accggataag gcgcagcggt cgggctgaac gggggggttcg    720
tgcacacagc ccagcttgga gcgaacgacc tacaccgaac tgagatacct acagcgtgag    780
ctatgagaaa gcgccacgct tcccgaaggg agaaaggcgg acaggtatcc ggtaagcggc    840
agggtcggaa caggagagcg cacgagggag cttccagggg gaaacgcctg gtatctttat    900
agtcctgtcg ggtttcgcca cctctgactt gagcatcgat ttttgtgatg ctcgtcaggg    960
gggcggagcc tatggaaaaa cgccagcaac gcagaaaggc ccaccgaag gtgagccagg   1020
tgattacatt tgggccctca tcagaggttt tcaccgtcat caccgaaacg cgcgaggcag   1080
ctgcggtaaa gctcatcagc gtggtcgtga agcgattcac agatgtctgc ctgttcatcc   1140
gcgtccagct cgttgagttt ctccagaagc gttaatgtct ggcttctgat aaagcgggcc   1200
atgttaaggc cggtttttc ctgtttggtc atttagaaaa actcatcgag catcaagtga    1260
aactgcaatt tattcatatc aggattatca ataccatatt tttgaaaaag ccgtttctgt   1320
aatgaaggag aaaactcacc gaggcagttc cataggatgg caagatcctg gtatcggtct   1380
gcgattccga ctcgtccaac atcaatacaa cctattaatt tcccctcgtc aaaaataagg   1440
ttatcaagtg agaaatcacc atgagtgacg actgaatccg gtgagaatgg caaaagctta   1500
tgcatttctt tccagacttg ttcaacaggc cagccattac gctcgtcatc aaaatcactc   1560
gcaccaacca aaccgttatt cattcgtgat tgcgcctgag cgagacgaaa tacgcgatcg   1620
ccgttaaaag gacaattaca acaggaatc gaatgcaacc ggcgcaggaa cactgccagc   1680
gcatcaacaa tattttcacc tgaatcagga tattcttcta atacctggaa tgctgttttc   1740
cctgggatcg cagtggtgag taaccatgca tcatcaggag tacggataaa atgcttgatg   1800
gtcggaagag gcataaattc cgtcagccag tttagcctga ccatctcatc tgtaacatca   1860
ttggcaacgc taccttttgcc atgtttcaga acaactctg gcgcatcggg cttcccatac   1920
aatcgataga ttgtcgcacc tgattgcccg acattatcgc gagcccattt atacccatat   1980
aaatcagcat ccatgttgga atttaatcgc ggcctcgagc aagacgtttc ccgttgaata   2040
tggctcatag ctcctgaaaa tctcgataac tcaaaaaata cgcccggtag tgatcttatt   2100
tcattatggt gaaagttgga acctcttacg tgccgatcaa gtcaaaagcc tccggtcgga   2160
ggcttttgac tttctgctat ggaggtcagg tatgatttaa atggtcagta ttgagcgata   2220
tctagagaat tcgtc                                                    2235
```

<210> SEQ ID NO 8
<211> LENGTH: 2652
<212> TYPE: DNA
<213> ORGANISM: Enterobacteria phage T7
<220> FEATURE:
<221> NAME/KEY: CDS
<222> LOCATION: (1)..(2649)

<400> SEQUENCE: 8

```
atg aac acg att aac atc gct aag aac gac ttc tct gac atc gaa ctg    48
Met Asn Thr Ile Asn Ile Ala Lys Asn Asp Phe Ser Asp Ile Glu Leu
1               5                  10                  15
```

| | | |
|---|---|---|
| gct gct atc ccg ttc aac act ctg gct gac cat tac ggt gag cgt tta<br>Ala Ala Ile Pro Phe Asn Thr Leu Ala Asp His Tyr Gly Glu Arg Leu<br>20              25                  30 | | 96 |
| gct cgc gaa cag ttg gcc ctt gag cat gag tct tac gag atg ggt gaa<br>Ala Arg Glu Gln Leu Ala Leu Glu His Glu Ser Tyr Glu Met Gly Glu<br>    35                  40                  45 | | 144 |
| gca cgc ttc cgc aag atg ttt gag cgt caa ctt aaa gct ggt gag gtt<br>Ala Arg Phe Arg Lys Met Phe Glu Arg Gln Leu Lys Ala Gly Glu Val<br>50              55                  60 | | 192 |
| gcg gat aac gct gcc gcc aag cct ctc atc act acc cta ctc cct aag<br>Ala Asp Asn Ala Ala Ala Lys Pro Leu Ile Thr Thr Leu Leu Pro Lys<br>65              70                  75                  80 | | 240 |
| atg att gca cgc atc aac gac tgg ttt gag gaa gtg aaa gct aag cgc<br>Met Ile Ala Arg Ile Asn Asp Trp Phe Glu Glu Val Lys Ala Lys Arg<br>            85                  90                  95 | | 288 |
| ggc aag cgc ccg aca gcc ttc cag ttc ctg caa gaa atc aag ccg gaa<br>Gly Lys Arg Pro Thr Ala Phe Gln Phe Leu Gln Glu Ile Lys Pro Glu<br>        100                 105                 110 | | 336 |
| gcc gta gcg tac atc acc att aag acc act ctg gct tgc cta acc agt<br>Ala Val Ala Tyr Ile Thr Ile Lys Thr Thr Leu Ala Cys Leu Thr Ser<br>            115                 120                 125 | | 384 |
| gct gac aat aca acc gtt cag gct gta gca agc gca atc ggt cgg gcc<br>Ala Asp Asn Thr Thr Val Gln Ala Val Ala Ser Ala Ile Gly Arg Ala<br>130                 135                 140 | | 432 |
| att gag gac gag gct cgc ttc ggt cgt atc cgt gac ctt gaa gct aag<br>Ile Glu Asp Glu Ala Arg Phe Gly Arg Ile Arg Asp Leu Glu Ala Lys<br>145                 150                 155                 160 | | 480 |
| cac ttc aag aaa aac gtt gag gaa caa ctc aac aag cgc gta ggg cac<br>His Phe Lys Lys Asn Val Glu Glu Gln Leu Asn Lys Arg Val Gly His<br>                165                 170                 175 | | 528 |
| gtc tac aag aaa gca ttt atg caa gtt gtc gag gct gac atg ctc tct<br>Val Tyr Lys Lys Ala Phe Met Gln Val Val Glu Ala Asp Met Leu Ser<br>            180                 185                 190 | | 576 |
| aag ggt cta ctc ggt ggc gag gcg tgg tct tcg tgg cat aag gaa gac<br>Lys Gly Leu Leu Gly Gly Glu Ala Trp Ser Ser Trp His Lys Glu Asp<br>        195                 200                 205 | | 624 |
| tct att cat gta gga gta cgc tgc atc gag atg ctc att gag tca acc<br>Ser Ile His Val Gly Val Arg Cys Ile Glu Met Leu Ile Glu Ser Thr<br>210                 215                 220 | | 672 |
| gga atg gtt agc tta cac cgc caa aat gct ggc gta gta ggt caa gac<br>Gly Met Val Ser Leu His Arg Gln Asn Ala Gly Val Val Gly Gln Asp<br>225                 230                 235                 240 | | 720 |
| tct gag act atc gaa ctc gca cct gaa tac gct gag gct atc gca acc<br>Ser Glu Thr Ile Glu Leu Ala Pro Glu Tyr Ala Glu Ala Ile Ala Thr<br>                245                 250                 255 | | 768 |
| cgt gca ggt gcg ctg gct ggc atc tct ccg atg ttc caa cct tgc gta<br>Arg Ala Gly Ala Leu Ala Gly Ile Ser Pro Met Phe Gln Pro Cys Val<br>            260                 265                 270 | | 816 |
| gtt cct cct aag ccg tgg act ggc att act ggt ggc ggc tat tgg gct<br>Val Pro Pro Lys Pro Trp Thr Gly Ile Thr Gly Gly Gly Tyr Trp Ala<br>        275                 280                 285 | | 864 |
| aac ggt cgt cgt cct ctg gcg ctg gtg cgt act cac agt aag aaa gca<br>Asn Gly Arg Arg Pro Leu Ala Leu Val Arg Thr His Ser Lys Lys Ala<br>290                 295                 300 | | 912 |
| ctg atg cgc tac gaa gac gtt tac atg cct gag gtg tac aaa gcg att<br>Leu Met Arg Tyr Glu Asp Val Tyr Met Pro Glu Val Tyr Lys Ala Ile<br>305                 310                 315                 320 | | 960 |
| aac att gcg caa aac acc gca tgg aaa atc aac aag aaa gtc cta gcg<br>Asn Ile Ala Gln Asn Thr Ala Trp Lys Ile Asn Lys Lys Val Leu Ala<br>                325                 330                 335 | | 1008 |

```
gtc gcc aac gta atc acc aag tgg aag cat tgt ccg gtc gag gac atc      1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac      1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg      1152
Met Asn Pro Glu Ala Leu Thr Ala Trp Lys Arg Ala Ala Ala Ala Val
370                 375                 380 tac cgc aag gac aag gct cgc aag tct cgc gtt atc agc ctt gag ttc      1200
Tyr Arg Lys Asp Lys Ala Arg Lys Ser Arg Ile Ile Ser Leu Glu Phe
385                 390                 395                 400 atg ctt gag caa gcc aat aag ttt gct aac cat aag gcc atc tgg ttc      1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc      1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa      1344
Asn Pro Gln Gly Asn Asp Met Thr Lys Gly Leu Leu Thr Leu Ala Lys
            435                 440                 445 ggt aaa cca atc ggt aag gaa ggt tac tac tgg ctg aaa atc cac ggt      1392
Gly Lys Pro Ile Gly Lys Glu Gly Tyr Tyr Trp Leu Lys Ile His Gly
450                 455                 460 gca aac tgt gcg ggt gtc gat aag gtt ccg ttc cct gag cgc atc aag      1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca      1488
Phe Ile Glu Glu Asn His Glu Asn Ile Met Ala Cys Ala Lys Ser Pro
            485                 490                 495 ctg gag aac act tgg tgg gct gag caa gat tct ccg ttc tgc ttc ctt      1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat      1584
Ala Phe Cys Phe Glu Tyr Ala Gly Val Gln His His Gly Leu Ser Tyr
            515                 520                 525 aac tgc tcc ctt ccg ctg gcg ttt gac ggg tct tgc tct ggc atc cag      1632
Asn Cys Ser Leu Pro Leu Ala Phe Asp Gly Ser Cys Ser Gly Ile Gln
530                 535                 540 cac ttc tcc gcg atg ctc cga gat gag gta ggt ggt cgc gcg gtt aac      1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag      1728
Leu Leu Pro Ser Glu Thr Val Gln Asp Ile Tyr Gly Ile Val Ala Lys
            565                 570                 575 aaa gtc aac gag att cta caa gca gac gca atc aat ggg acc gat aac      1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa      1824
Glu Val Val Thr Val Thr Asp Glu Asn Thr Gly Glu Ile Ser Glu Lys
            595                 600                 605 gtc aag ctg ggc act aag gca ctg gct ggt caa tgg ctg gct tac ggt      1872
Val Lys Leu Gly Thr Lys Ala Leu Ala Gly Gln Trp Leu Ala Tyr Gly
            610                 615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag      1968
Ser Lys Glu Phe Gly Phe Arg Gln Gln Val Leu Glu Asp Thr Ile Gln
                        645                 650                 655
```

```
cca gct att gat tcc ggc aag ggt ctg atg ttc act cag ccg aat cag    2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg    2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag    2112
Val Val Ala Ala Val Glu Ala Met Asn Trp Leu Lys Ser Ala Ala Lys
690                 695                 700 ctg ctg gct gct gag gtc aaa gat aag aag act gga gag att ctt cgc    2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg    2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc    2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag    2304
Gly Gln Phe Arg Leu Gln Pro Thr Ile Asn Thr Asn Lys Asp Ser Glu
        755                 760                 765 att gat gca cac aaa cag gag tct ggt atc gct cct aac ttt gta cac    2352
Ile Asp Ala His Lys Gln Glu Ser Gly Ile Ala Pro Asn Phe Val His
770                 775                 780 agc caa gac ggt agc cac ctt cgt aag act gta gtg tgg gca cac gag    2400
Ser Gln Asp Gly Ser His Leu Arg Lys Thr Val Val Trp Ala His Glu
785                 790                 795                 800 aag tac gga atc gaa tct ttt gca ctg att cac gac tcc ttc ggt acc    2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg    2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag    2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt    2592
Phe Ala Asp Gln Leu His Glu Ser Gln Leu Asp Lys Met Pro Ala Leu
850                 855                 860 ccg gct aaa ggt aac ttg aac ctc cgt gac atc tta gag tcg gac ttc    2640
Pro Ala Lys Gly Asn Leu Asn Leu Arg Asp Ile Leu Glu Ser Asp Phe
865                 870                 875                 880 gcg ttc gcg taa                                                    2652
Ala Phe Ala <210> SEQ ID NO 9
<211> LENGTH: 883
<212> TYPE: PRT
<213> ORGANISM: Enterobacteria phage T7

<400> SEQUENCE: 9

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60
```

```
Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala
```